(12) United States Patent
Ohashi et al.

(10) Patent No.: US 11,439,543 B2
(45) Date of Patent: Sep. 13, 2022

(54) WEARABLE ARTICLE EQUIPPED WITH SENSOR

(71) Applicant: Kao Corporation, Tokyo (JP)

(72) Inventors: Kazuo Ohashi, Koshigaya (JP); Hideko Goshowaki, Shibuya-ku (JP); Mayumi Nagaosa, Utsunomiya (JP)

(73) Assignee: Kao Corporation, Tokyo (JP)

( * ) Notice: Subject to any disclaimer, the term of this patent is extended or adjusted under 35 U.S.C. 154(b) by 445 days.

(21) Appl. No.: 16/605,263

(22) PCT Filed: May 29, 2018

(86) PCT No.: PCT/JP2018/020606
§ 371 (c)(1),
(2) Date: Oct. 15, 2019

(87) PCT Pub. No.: WO2018/221530
PCT Pub. Date: Dec. 6, 2018

(65) Prior Publication Data
US 2020/0121516 A1 Apr. 23, 2020

(30) Foreign Application Priority Data

May 30, 2017 (JP) .............................. JP2017-107253
May 30, 2017 (JP) .............................. JP2017-107254
Jul. 7, 2017 (JP) .............................. JP2017-134129

(51) Int. Cl.
*A61F 13/42* (2006.01)
*G01V 3/08* (2006.01)
(52) U.S. Cl.
CPC ................ *A61F 13/42* (2013.01); *G01V 3/08* (2013.01); *A61F 2013/424* (2013.01)

(58) Field of Classification Search
CPC ...... A61F 13/42; A61F 2013/424; A61F 5/44; A61F 5/451; A61F 13/49413; A61F 13/511; G01V 3/08
See application file for complete search history.

(56) References Cited

U.S. PATENT DOCUMENTS 6,093,869 A 7/2000 Roe et al.
7,522,477 B1 4/2009 Sheldon
(Continued)

FOREIGN PATENT DOCUMENTS

CN 1226855 A 8/1999
CN 101217923 A 7/2008
(Continued)

OTHER PUBLICATIONS

International Search Report dated Aug. 21, 2018 in PCT/JP2018/020606 filed on May 29, 2018.
(Continued)

*Primary Examiner* — Adnan Aziz
(74) *Attorney, Agent, or Firm* — Oblon, McClelland, Maier & Neustadt, L.L.P.

(57) ABSTRACT

A urination sensor includes: a printing substrate made of a resin film; and a plurality of planar printed electrodes made by an electroconductive ink applied to the printing substrate. The urination sensor is provided with a section where the printing substrate is not present, the section being provided between the plurality of planar printed electrodes. The urination sensor, including the section where the printing substrate is not present, is covered by a cover sheet. A backsheet is an electrically insulating, sparingly liquid-permeable substrate, and the printing substrate is an electrically insulating substrate. Non-application sections are present on the surface of the cover sheet to which an adhesive is applied, and the section where the printing substrate is not present forms an air-passage opening which
(Continued)

retains an air-passage function with the non-application sections where the adhesive is not applied.

9 Claims, 7 Drawing Sheets

(56) References Cited

U.S. PATENT DOCUMENTS

| | | | |
|---|---|---|---|
| 8,739,397 B2* | 6/2014 | Nagata | A61B 5/282 29/829 |
| 9,675,496 B1 | 6/2017 | Alkhamis | |
| 2007/0035405 A1 | 2/2007 | Wada et al. | |
| 2007/0191807 A1* | 8/2007 | Hayashi | A61F 13/49413 604/385.101 |
| 2008/0243099 A1 | 10/2008 | Tippey | |
| 2008/0297325 A1 | 12/2008 | Torstensson et al. | |
| 2011/0172625 A1* | 7/2011 | Wada | A61F 13/42 604/385.01 |
| 2012/0232508 A1* | 9/2012 | Urushihara | A61F 13/539 604/372 |
| 2012/0245542 A1 | 9/2012 | Suzuki et al. | |
| 2013/0018231 A1 | 1/2013 | Hong et al. | |
| 2013/0036802 A1 | 2/2013 | Johnson et al. | |
| 2013/0303867 A1 | 11/2013 | Elfstrom et al. | |
| 2014/0182051 A1 | 7/2014 | Tanimoto et al. | |
| 2014/0292520 A1 | 10/2014 | Carney et al. | |
| 2014/0333442 A1 | 11/2014 | Carney | |
| 2015/0080819 A1 | 3/2015 | Charna et al. | |
| 2015/0148762 A1 | 5/2015 | Johnson et al. | |
| 2015/0206151 A1 | 7/2015 | Carney et al. | |
| 2016/0078176 A1 | 3/2016 | Ranta | |
| 2016/0310329 A1 | 10/2016 | Patel | |
| 2019/0110938 A1 | 4/2019 | Chiu | |
| 2020/0352794 A1* | 11/2020 | Curran | A61F 13/42 |

FOREIGN PATENT DOCUMENTS

| | | |
|---|---|---|
| CN | 101340876 A | 1/2009 |
| CN | 102054334 A | 5/2011 |
| CN | 202650203 U | 1/2013 |
| CN | 104224448 A | 12/2014 |
| EP | 1 213 273 A2 | 7/2002 |
| EP | 2 091 489 A1 | 8/2009 |
| JP | 2002-73805 A | 3/2002 |
| JP | 3666473 B2 | 6/2005 |
| JP | 410143282 | 6/2008 |
| JP | 2012-105839 A | 8/2012 |
| JP | 2012-152249 A | 8/2012 |
| JP | 2013-39158 A | 2/2013 |
| JP | 2015-506192 A | 3/2015 |
| JP | 2015-119784 A | 7/2015 |
| JP | 2015-534153 A | 11/2015 |
| JP | 2016-32519 A | 3/2016 |
| JP | 2016-32520 A | 3/2016 |
| JP | 2016-195702 A | 11/2016 |
| JP | 2017-189340 A | 10/2017 |
| JP | 2017-189348 A | 10/2017 |
| JP | 2017-207317 A | 11/2017 |
| TW | 410155 B | 11/2000 |
| TW | 201130468 A | 9/2011 |
| TW | 201302174 A | 1/2013 |
| TW | 201312104 A1 | 3/2013 |
| TW | M515375 U | 1/2018 |
| WO | WO 97/42613 A2 | 11/1997 |
| WO | WO 98/01227 A1 | 1/1998 |
| WO | WO 02/101679 | 12/2002 |
| WO | WO 2007/128038 A1 | 11/2007 |
| WO | WO 2009/001229 A2 | 12/2008 |
| WO | WO 2009/027871 A1 | 3/2009 |
| WO | WO 2010/001274 A2 | 1/2010 |
| WO | WO 2011/156862 A1 | 12/2011 |
| WO | WO 2013/022742 A1 | 2/2013 |
| WO | WO 2013/095230 A1 | 6/2013 |
| WO | WO 2013/095231 A1 | 6/2013 |
| WO | WO 2014/035302 A1 | 3/2014 |
| WO | WO 2014/064680 A1 | 5/2014 |
| WO | WO 2014/178763 A1 | 11/2014 |

OTHER PUBLICATIONS

Extended European Search Report dated Feb. 2, 2021 in European Patent Application No. 16809573.1, 5 pages.
International Search Report dated Aug. 21, 2018 in PCT/JP2018/020615, citing documents AJ, AO and AP therein, 1 page.
Margaret Heale, Continence Assessment, Types of Incontinence, and Care Planning (Year: 2019).
Omli et al., Pad per day usage, urinary incontinence and urinary tract infections in nursing home residents (Year: 2010).
Rice et al., Rationale and Design of a Novel Method to Assess the Usability of Body-Worn Absorbent Incontinence Care Products by Caregivers (Year: 2018).

* cited by examiner (a)

(b)

WEARABLE ARTICLE EQUIPPED WITH SENSOR

CROSS REFERENCE TO RELATED APPLICATIONS

This application is a national phase application of PCT/JP2018/020606, filed May 29, 2018, which claims priority to Japanese Patent Application No. 2017-107253, filed May 30, 2017; Japanese Patent Application No. 2017-107254, filed May 30, 2017, and Japanese Patent Application No. 2017-134129, filed Jul. 7, 2017, the entire content and disclosure of each of which is incorporated by reference into the present application.

TECHNICAL FIELD

The present invention relates to a sensor-equipped wearable article, and more specifically, to a sensor-equipped wearable article including a urination sensor that detects urination and that is attached to one of a plurality of sheets constituting the wearable article.

BACKGROUND ART

The recent aging of society has caused an increase in occasions requiring, for example, nursing of bedridden care-receivers in hospitals, nursing-care facilities, and the like. Appropriate management of urination is necessary for nursing bedridden care-receivers. Particularly in cases where the care-receiver cannot urinate by himself/herself and needs to wear a liquid-absorbent wearable article such as a diaper, it is necessary to monitor the urination of the care-receiver and more appropriately manage, for example, the time for changing the wearable article.

As a method for managing urination of a care-receiver wearing a diaper etc., institutions such as hospitals and nursing-care facilities generally adopt a method in which a caregiver, such as a nurse, makes the rounds at predetermined times at a frequency of around 6 to 8 times a day, for example, and checks whether the care-receiver has urinated or not and changes diapers when necessary. This management method, however, is inefficient, as the care-receiver may not have urinated when the caregiver made the rounds. Further, an increase in the number of care-receivers will increase the burden on the caregiver. This method is also problematic from the care-receiver's perspective, in that, for example, if the care-receiver urinates immediately after the caregiver's round and his/her diaper is left unchanged until the next round, the care-receiver will be left in an uncomfortable and insanitary state.

In view of the above, a urination detection device has been developed, wherein a plurality of sensor elements are attached to a wearable article, such as a diaper, to be worn by a care-receiver, and the wearer's urination is detected by the sensor elements and a caregiver can be notified through a nurse call system etc. when the wearer has urinated (see, for example, Patent Literature 1). The urination detection device of Patent Literature 1 is capable of measuring the urine absorption amount and urination amount from the spreading of urine absorbed by the liquid-absorbent wearable article at the time of urination.

Regarding the urination detection device of Patent Literature 1, it is described that there is a high correlativity between the amount of change in output by a capacitance sensor and the spreading area of urine in the wearable article and there is also a high correlativity between the spreading area of urine in the wearable article and the urine absorption amount, and that the amount of urine per second (urine flow rate) can be calculated. However, the demonstration results by this device are only at a laboratory level. Therefore, if the urination detection device of Patent Literature 1 is to be put to practical use in a hospital or a nursing-care facility, it will be necessary to further study, for example, how it would be practical to provide a plurality of sensor elements to a wearable article, such as a diaper, to be worn by a wearer such as a care-receiver. Against such a backdrop, there has been developed a wearable article wherein sensor elements made of a plurality of electrode groups are provided, for example, by applying an electroconductive ink including an electroconductive material on a surface of one of a plurality of sheets constituting a wearable article (see, for example, Patent Literature 2).

Other than the urination detection device disclosed in Patent Literature 1 and the wearable article disclosed in Patent Literature 2, there have been developed, as urination detection means for detecting whether or not a wearer has urinated, techniques enabling the detection of urination by causing a plurality of sensor elements to be short-circuited by urine, as in the absorbent articles disclosed in Patent Literatures 3 to 5.

CITATION LIST

Patent Literature

Patent Literature 1: JP 2013-39158A
Patent Literature 2: JP 2015-119784A
Patent Literature 3: International Publication WO98/1227
Patent Literature 4: International Publication WO2009/001229
Patent Literature 5: International Publication WO2011/156862

SUMMARY OF INVENTION

The present invention is a sensor-equipped wearable article including a urination sensor that detects urination and that is attached to an outside surface of one sheet among a plurality of sheets constituting the wearable article. The urination sensor includes: a printing substrate formed of a resin film; and a plurality of planar printed electrodes that constitute a sensor element and that are made by an electroconductive ink applied to a surface of the printing substrate. The urination sensor is provided with a section where the printing substrate is not present, the section being provided between the plurality of planar printed electrodes. The urination sensor, including the section where the printing substrate is not present, is covered by a cover sheet in which an adhesive is applied to a nonwoven fabric. The printing substrate is bonded to the one sheet by the adhesive applied to the cover sheet in a manner that the printed electrodes face the surface of the one sheet. The one sheet is an electrically insulating, sparingly liquid-permeable substrate. The printing substrate is an electrically insulating substrate. The plurality of planar printed electrodes are covered by the one sheet and the printing substrate. Non-application sections are present on the surface of the cover sheet to which the adhesive is applied, and the section where the printing substrate is not present forms an air-passage opening which retains an air-passage function with the non-application sections.

DESCRIPTION OF EMBODIMENTS

The wearable article disclosed in Patent Literature 2 is capable of measuring the spreading of body fluid with high accuracy. However, the sheet to which the electroconductive ink is applied is likely to shrink by the heat at the time of drying the electroconductive ink, and thus, the wearable article is difficult to manufacture. Thus, there has been a demand to develop a novel wearable article that is provided with a urination sensor for detecting urination and that can be manufactured more easily by suppressing sheet shrinkage at the time of drying the electroconductive ink.

On the other hand, the absorbent articles disclosed in Patent Literatures 3 to 5 do not require insulation of the plurality of sensor elements, in contrast to cases of detecting the amount of change in output by a capacitance sensor. Thus, Patent Literatures 3 to 5 do not give consideration to air permeability in locations where the sensor elements are provided.

The present invention relates to a sensor-equipped wearable article, wherein variations in the detection of urination amounts detected by a urination sensor can be suppressed effectively by preventing sheet shrinkage at the time of drying an electroconductive ink, and wherein a urination sensor using an electroconductive ink can be provided easily. The present invention also relates to a sensor-equipped wearable article, wherein urination amounts can be detected with high accuracy without impairing air permeability.

The present invention is a sensor-equipped wearable article including a urination sensor that detects urination and that is attached to an outside surface of one sheet among a plurality of sheets constituting the wearable article. The urination sensor includes a printing substrate formed of a resin film, and a plurality of planar printed electrodes that constitute a sensor element and that are made by an electroconductive ink applied to a surface of the printing substrate. The urination sensor is provided with a section where the printing substrate is not present, the section being provided between the plurality of planar printed electrodes. The urination sensor, including the section where the printing substrate is not present, is covered by a cover sheet in which an adhesive is applied to a nonwoven fabric. The printing substrate is bonded to the one sheet by the adhesive applied to the cover sheet in a manner that the printed electrodes face the surface of the one sheet. The one sheet is an electrically insulating, sparingly liquid-permeable substrate. The printing substrate is an electrically insulating substrate. The plurality of planar printed electrodes are covered by the one sheet and the printing substrate. Non-application sections are present on the surface of the cover sheet to which the adhesive is applied, and the section where the printing substrate is not present forms an air-passage opening which retains an air-passage function with the non-application sections.

Figure 1:
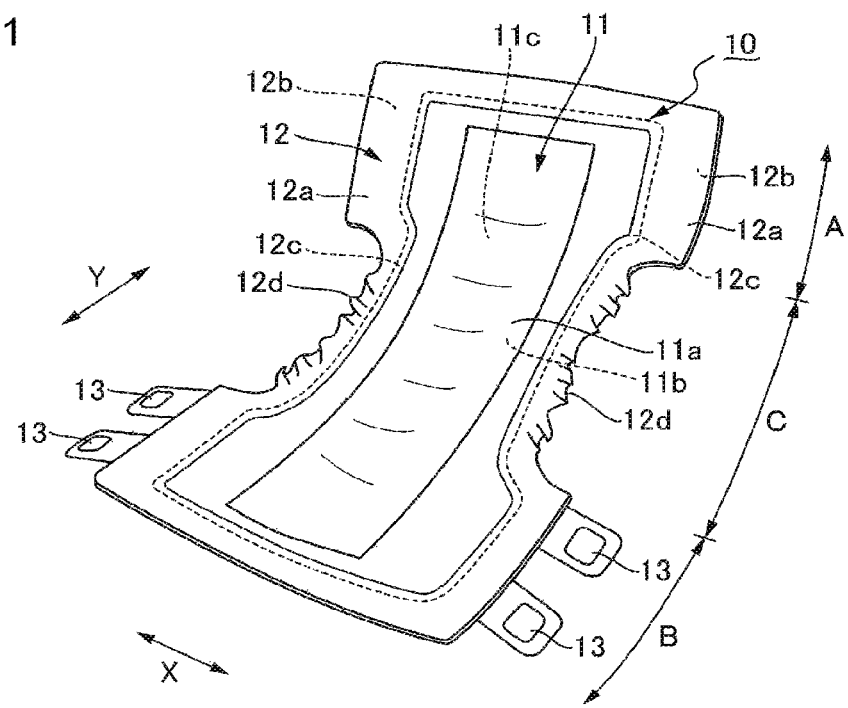
FIG. 1 is a schematic perspective view of a urine absorption pad, which is a sensor-equipped wearable article according to a preferred embodiment of the present invention, in a state employed in combination with a disposable diaper.
Figure 2:
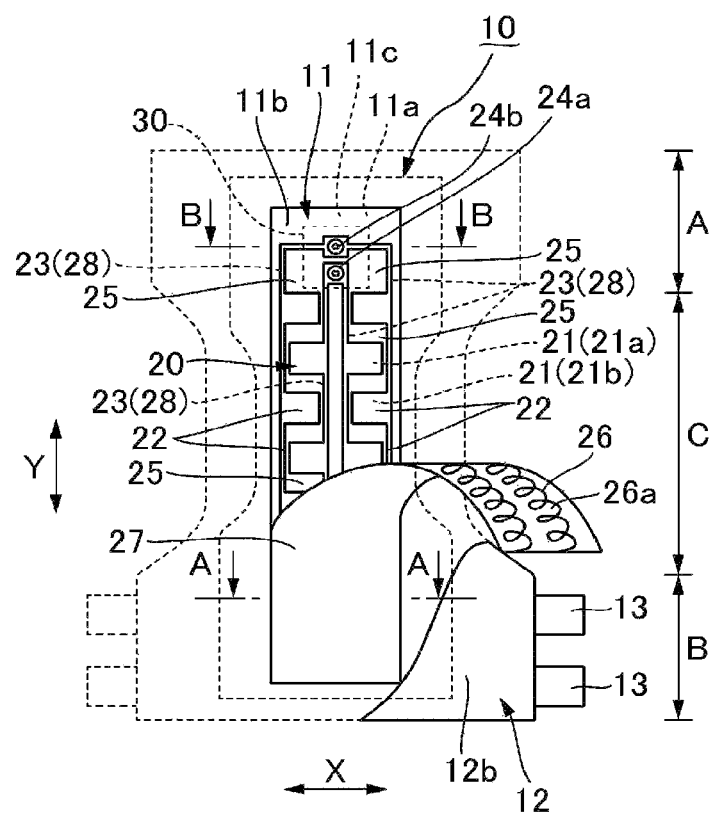
FIG. 2 is a back-side view of a urination sensor attached to the urine absorption pad, illustrated in a state where a portion of a cover sheet covering the urination sensor has been peeled, the urine absorption pad being viewed from the non-skin-facing surface side.

FIG. 1 illustrates a sensor-equipped wearable article 10 according to a preferred embodiment of the present invention. The sensor-equipped wearable article includes, for example, a urination sensor 20 attached to a urine absorption pad 11 which is an absorbent article having liquid-absorbing properties, and is used in combination with a disposable diaper (diaper main body) 12. As illustrated in FIG. 2, in the present embodiment, the urine absorption pad 11 includes an absorbent member 11c which is oblong in the longitudinal direction (see FIGS. 3(a) and 3(b)). In the present embodiment, one sheet, among a plurality of sheets constituting the sensor-equipped wearable article 10, is the urine absorption pad 11's backsheet 11b arranged on the outer side (the non-skin-facing surface side) on the opposite side from the skin-facing surface side which comes into contact with the wearer's skin, and the urination sensor 20 is attached to the outside surface of the backsheet. The urination sensor 20 includes sensor elements constituted by a plurality of planar printed electrodes 21 (see FIG. 2 and FIG. 3(a)) formed by applying an electroconductive ink to a printing substrate 22. The urination sensor 20 can detect the spreading of urine absorbed by the urine absorption pad 11 on the basis of changes in impedance between the plurality of planar printed electrodes 21. In the present embodiment, by applying the electroconductive ink to the printing substrate 22, the backsheet 11b is prevented from shrinking caused by drying the applied electroconductive ink at the time of forming the printed electrodes 21, and thus, the urination sensor 20 using the electroconductive ink can be provided easily and efficiently to the urine absorption pad 11.

Figure 3:
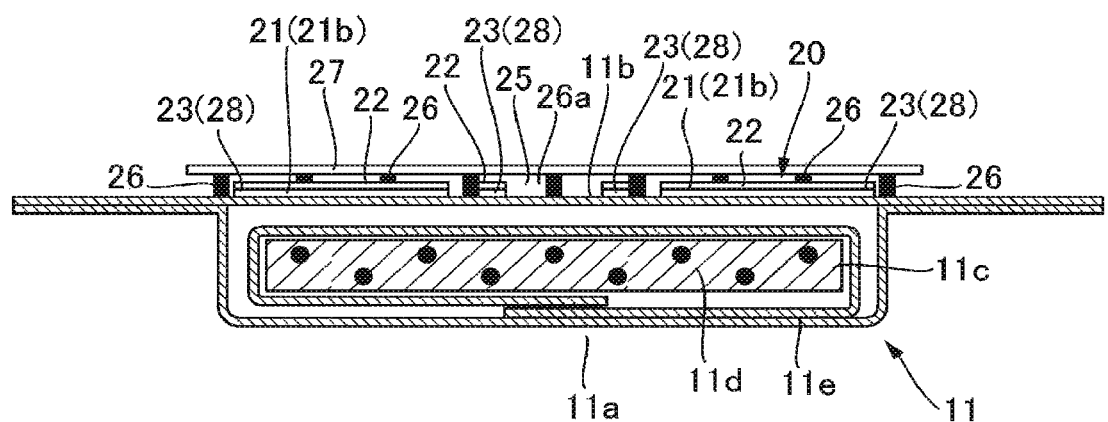
FIG. 3(a) is an enlarged schematic cross-sectional view taken along line A-A of FIG. 2, illustrating the urine absorption pad with the urination sensor and the cover sheet attached thereto.
FIG. 3(b) is an enlarged schematic cross-sectional view taken along line B-B of FIG. 2.
Figure 3:
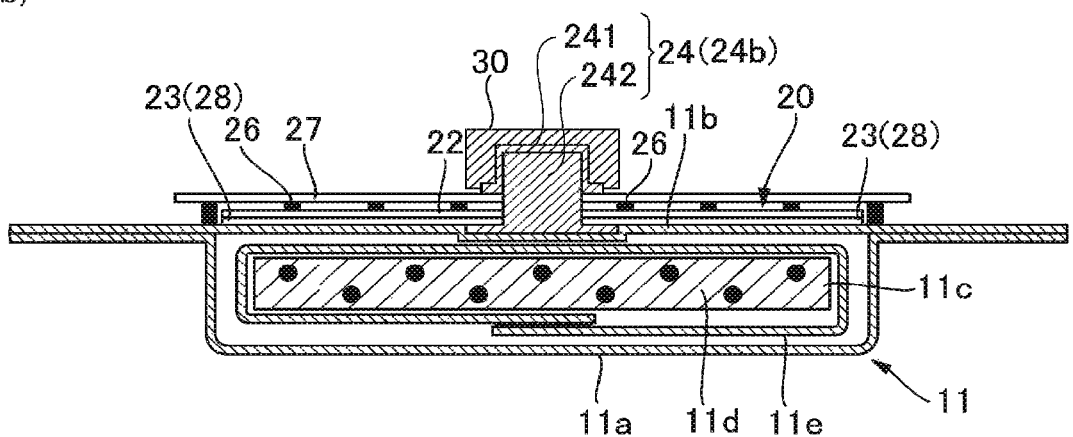
Figure 4:
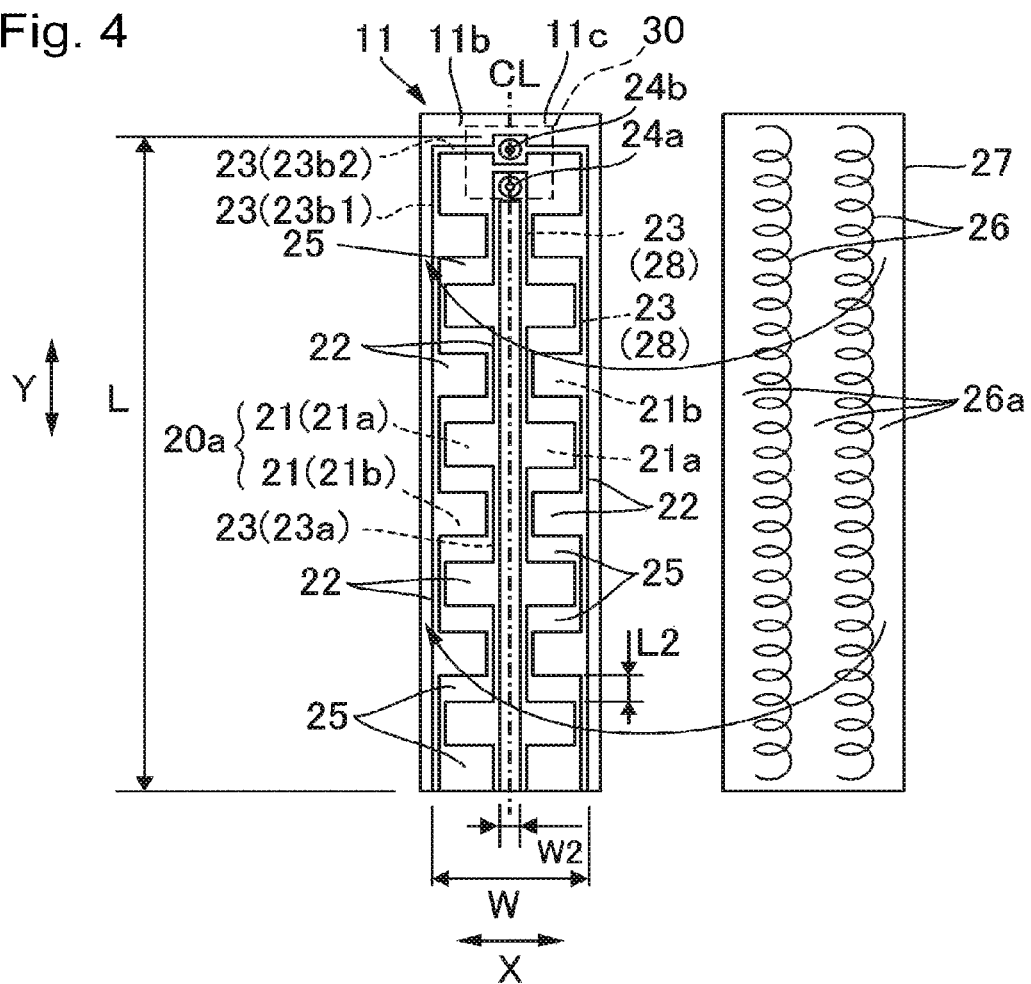
FIG. 4 is a back-side view of the cover sheet and the urine absorption pad provided with the urination sensor in a state before the cover sheet is attached, the back-side view illustrating the urination sensor provided to the urine absorption pad and the cover sheet to be attached so as to cover the urination sensor.

Preferably, the sensor-equipped wearable article 10 of the present embodiment is an article integrated by using, in combination: the urine absorption pad 11 in which the urination sensor 20 for detecting urination is attached, for example, to the urine absorption pad 11's backsheet 11b serving as one of the plurality of sheets constituting the wearable article 10; and a disposable diaper 12 serving as an outer member. As illustrated in FIGS. 2 to 4, the urination sensor 20 includes, for example: a printing substrate 22 formed of an electrically insulating polyethylene terephthalate film; and a plurality of planar printed electrodes 21 that constitute sensor elements and that are made by an electroconductive ink applied to a surface of the printing substrate 22. The urination sensor 20 is provided with a section where the printing substrate 22 is not present, the section being provided between the plurality of planar printed electrodes 21, and the urination sensor, including the section where the printing substrate 22 is not present, is covered by a cover sheet 27 in which an adhesive 26 is applied to a nonwoven fabric. The urination sensor is bonded by the adhesive 26 applied to the cover sheet 27 in a manner that the printed electrodes 21 face the surface of the backsheet 11b. In the sensor-equipped wearable article 10, the urination sensor 20 is covered by the cover sheet 27 made of a nonwoven fabric to which the adhesive 26 is applied (see FIGS. 2 and 4), and the printing substrate 22 is bonded to the backsheet 11b by the adhesive 26 applied to the cover sheet 27 in a manner that the printed electrodes 21 face the surface of the backsheet 11b. The adhesive 26 is applied to the surface of the cover sheet 27 in a spiral-shaped application pattern, for example (see FIGS. 2 and 4). Thus, on the surface of the cover sheet 27, non-application sections 26a are formed in the gaps formed between the spirally applied adhesive 26 and in outer peripheral sections. The backsheet 11b, serving as the one sheet, is an electrically insulating, sparingly liquid-permeable substrate. The printing substrate 22 is an electrically insulating substrate. The plurality of planar printed electrodes 21 are covered by the backsheet 11b and the printing substrate 22, preferably together with later-described conducting wire portions 23. Since non-application sections 26a are present on the surface of the cover sheet 27 to which the adhesive 26 is applied, the section where the printing substrate 22 is not present forms an air-passage opening 25 which retains an air-passage function with the non-application sections 26a. The top-surface side of the urine absorption pad 11 may be provided with auxiliary side sheets (not illustrated) for forming leak-proof cuffs (not illustrated), for example.

In the present embodiment, preferably, the plurality of planar printed electrodes 21 are connected by conducting wire portions 23. Preferably, the electroconductive ink is an ink made by blending a metal powder, such as silver powder, as an electroconductive substance. Like the printed electrodes 21, the conducting wire portions 23 are made of a printed electroconductive layer 28 (see FIGS. 3(a) and 3(b)) formed by the electroconductive ink applied to the surface of the printing substrate 22.

In the present embodiment, as illustrated in FIG. 1, the diaper main body (disposable diaper) 12 to be used in combination with the urine absorption pad 11 to which the urination sensor 20 is attached has a structure similar to the disposable diaper disclosed in JP 2015-119784A. In FIG. 1, the urine absorption pad 11, serving as an inner member, is used in combination with the diaper main body (disposable diaper) 12, serving as an outer member. The diaper main body 12 includes: a main-body topsheet 12a having the urine absorption pad 11 attached to the inner, skin-facing surface side; a main-body backsheet 12b arranged most toward the non-skin-facing surface side; and a main-body absorbent member 12c arranged between the two sheets 12a, 12b. On the outer side of the main-body absorbent member 12c in the width direction X, the diaper main body 12 also includes main-body leg elastic members (not illustrated) which are for forming leg gathers and which are arranged in a stretched state in the longitudinal direction Y. The contraction of the main-body leg elastic members (not illustrated) forms leg gathers 12d. The top-surface side of the main-body topsheet 12a may be provided with auxiliary side sheets (not illustrated) etc. for forming leak-proof cuffs (not illustrated), for example.

The main-body absorbent member 12c of the diaper main body 12 has, for example, a larger planar-view shape than the urine absorption pad 11 attached so as to be superposed on the skin-facing surface side (inner side) of the diaper main body 12, and the left and right lateral side edge portions in the front region A and the left and right lateral side edge portions in the rear region B extend more outward in the width direction X than the left and right lateral side edge portions in the crotch region C. The left and right lateral side edge portions in the crotch region C are arcuately curved inwardly in the width direction X, and the diaper main body, as a whole, has a shape in which the central portion, in the longitudinal direction Y, is narrowed inwardly. Like the later-described absorbent member 11c of the urine absorption pad 11, the main-body absorbent member 12c is formed by covering, with a single core-wrap sheet, an absorbent core in which water-absorbent polymer particles are retained in an aggregate of fibers, such as pulp fibers.

The main-body topsheet 12a and the main-body backsheet 12b both extend outward from the main-body absorbent member 12c's lateral side edge portions extending along the longitudinal direction and the main-body absorbent member's end edge portions extending along the width direction X. The main-body topsheet 12a and the main-body backsheet 12b are joined together by, for example, an adhesive or fusion-bonding in extension portions that extend outward from the peripheral edge of the main-body absorbent member 12c, and inside, the main-body absorbent member 12c is provided in a sandwiched and fixed state.

The diaper main body 12 formed as described above has, as a whole, a shape in which the central portion, in the longitudinal direction Y, is narrowed inwardly. The diaper main body 12 is a so-called open-type diaper, and two pairs of fastening tapes 13 are provided at the left and right lateral side edge portions in the rear region B. A landing tape (not illustrated) where the fastening tapes 13 are fastened is provided on the outside surface (non-skin-facing surface) in the front region A of the diaper main body 12. Note that, other than a disposable diaper, the outer member used in combination with the urine absorption pad 11 as the inner member may be cloth underpants or adult pull-up pants. Also, other than a urine absorption pad equipped with a sensor sheet, the sensor-equipped wearable article 10 may be a sensor-equipped disposable diaper (tape-fastening diaper or adult pull-up pants).

As illustrated in FIGS. 2 to 4, the urine absorption pad 11 attached so as to be superposed on the skin-facing surface side (inner side) of the diaper main body 12 includes: a liquid-permeable topsheet 11a arranged on the skin-facing surface side; a sparingly liquid-permeable backsheet 11b arranged on the non-skin-facing surface side; and an absorbent member 11c arranged between the two sheets 11a, 11b (see FIGS. 3(a) and 3(b)). The topsheet 11a, backsheet 11b, and absorbent member 11c of the urine absorption pad 11 have a rectangular shape that is long in the longitudinal direction Y of the sensor-equipped wearable article 10. The topsheet 11a and the backsheet 11b are both provided so as to extend outward from the absorbent member 11c's lateral side edge portions extending along the longitudinal direction Y and the absorbent member's end edge portions extending along the width direction X, and have a shape in which the central portion, in the longitudinal direction Y, is narrowed inwardly, like the main-body absorbent member 12c of the diaper main body 12. The topsheet 11a and the backsheet 11b are joined together, either directly or with a side sheet etc. interposed therebetween, by, for example, an adhesive or fusion-bonding in extension portions that extend outward from the peripheral edge of the absorbent member 11c, and inside, the absorbent member 11c is provided in a sandwiched and fixed state. Note that, as illustrated in FIGS. 3(a) and 3(b), the absorbent member 11c is formed by covering, with a single core-wrap sheet 11e, an absorbent core 11d in which water-absorbent polymer particles are retained in an aggregate of fibers, such as pulp fibers.

In the present embodiment, as described above, the urination sensor 20 for detecting urination is attached preferably to the urine absorption pad 11's backsheet 11b serving as one of the plurality of sheets constituting the wearable article 10. That is, in the present embodiment, a plurality of sensor elements 20a are formed in the urination sensor 20 by the plurality of planar printed electrodes 21 made by the electroconductive ink applied to the surface of the printing substrate 22, as described below. More specifically, as described below, the plurality of planar printed electrodes 21 include a plurality of positive electrodes 21a and a plurality of negative electrodes 21b, and the plurality of positive electrodes 21a and the plurality of negative electrodes 21b constitute the plurality of sensor elements 20a. By employing the sensor elements 20a constituted by the positive electrodes 21a and the negative electrodes 21b, the urination sensor 20 detects changes in impedance of the sensor elements 20a. On the basis of the detected changes in impedance, the sensor-equipped wearable article 10 can detect whether or not a wearer has urinated, and can measure or estimate the urine absorption amount and/or urination amount from the spreading of urine absorbed by the urine absorption pad 11 upon urination.

As illustrated in FIG. 4, in the present embodiment, there are eight planar printed electrodes 21 arranged along the longitudinal direction Y of the urine absorption pad 11 with intervals therebetween. The eight printed electrodes 21 (electrode array) arranged along the longitudinal direction Y with intervals therebetween have a configuration in which positive electrodes 21a and negative electrodes 21b are arranged alternately with interval therebetween, and the positive electrode 21a and the negative electrode 21b adjacent to one another in the longitudinal direction Y constitute the aforementioned sensor element 20a. The aforementioned sections where the printing substrate 22 is not present are provided at respective sections of the intervals between the positive electrodes 21a and the negative electrodes 21b. In the present embodiment, two rows of electrodes (electrode arrays), each including eight printed electrodes 21 arranged along the longitudinal direction Y with intervals therebetween, are arranged with a predetermined interval therebetween in the width direction X. As a whole, there are sixteen printed electrodes 21 dispersedly arranged uniformly in the width direction X and the longitudinal direction Y. As for the two printed electrodes 21 adjacent to one another in the width direction X, a positive electrode may be paired with a negative electrode, and a negative electrode may be paired with a positive electrode; in the present embodiment, however, a positive electrode is paired with a positive electrode, and a negative electrode is paired with a negative electrode. It should be noted that the number of printed electrodes 21 to be arranged is preferably from six to twelve in the longitudinal direction Y of the urine absorption pad 11.

As described above, in the present embodiment, the plurality of planar printed electrodes 21 are arranged in two rows along the longitudinal direction Y of the urine absorption pad 11, and a total of sixteen electrodes, eight in each electrode array, are arranged (see FIG. 4). In the eight printed electrodes 21 arranged in each electrode array, the four positive electrodes 21a and the four negative electrodes 21b arranged alternately in the longitudinal direction Y are connected respectively by conducting wire portions 23. More specifically, the four positive electrodes 21a in each electrode array are connected by conducting wire portions 23a arranged so as to extend linearly along the longitudinal direction Y on the inner side in the width direction X (i.e., closer to the center line CL); one end portion of the conducting wire portion 23 is connected to a terminal portion 24a provided at an end section in the longitudinal direction Y of the urine absorption pad 11. The four negative electrodes 21b in the respective electrode arrays are connected by conducting wire portions 23b1 arranged so as to extend linearly along the longitudinal direction Y on both lateral sides along the longitudinal direction Y of the urine absorption pad 11, and one end portion, in the longitudinal direction Y, of the respective conducting wire portions 23b1 is connected to one end portion of respective conducting wire portions 23b2 arranged so as to extend linearly in the width direction X. The other end of each conducting wire portion 23b2 is connected to a terminal portion 24b provided at an end section in the longitudinal direction Y of the urine absorption pad 11. The conducting wire portions 23a are configured so as to be arranged on the urination sensor 20's inner side (i.e., closer to the center line CL) in a planar view of the urination sensor 20. On the other hand, the conducting wire portions 23b1 are configured so as to be arranged on the outer sides of the plurality of positive electrodes 21a so as to surround the plurality of positive electrodes 21a in a planar view of the urination sensor 20. The plurality of negative electrodes 21b are grounded through the terminal portion 24b. By grounding the plurality of negative electrodes 21b arranged on the outer sides, the intrusion of external noise can be reduced in the urination sensor 20, and thus measurement accuracy can be improved.

Figure 5:
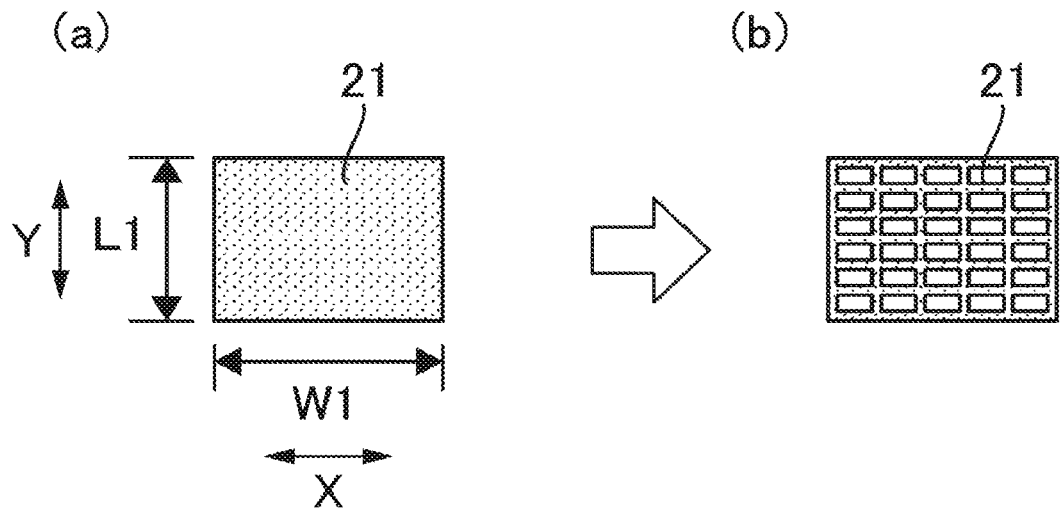
FIGS. 5(a) and 5(b) are enlarged plan views illustrating examples of forms of a printed electrode.

In the present embodiment, as described further below, the plurality of planar printed electrodes 21 constituting the urination sensor 20 are formed in a planar shape by applying an electroconductive ink on the surface of the printing substrate 22. As illustrated in FIG. 5(a), the printed electrodes 21 each have the same rectangular shape. Stated differently, the positive electrodes 21a and the negative electrodes 21b are formed in the same rectangular shape.

As illustrated in FIGS. 4 and 5(a), it is preferable that the percentage ((L1/L)×100) of the length L1, in the Y direction (same as the longitudinal direction Y of the urine absorption pad 11), of each printed electrode 21 (positive electrode 21a and negative electrode 21b) to the length L, in the longitudinal direction Y, of the printing substrate 22 is around 0.19 to 22%, and it is preferable that the percentage ((W1/W)× 100) of the length W1, in the X direction (same as the width direction X of the urine absorption pad 11 (see FIG. 4)), of each printed electrode 21 (positive electrode 21a and negative electrode 21b) to the length W, in the width direction X, of the printing substrate 22 is around 3 to 93%. More specifically, it is preferable that the length L, in the longitudinal direction Y, of the printing substrate 22 is around 380 to 532 mm, and it is preferable that the length L1, in the Y direction, of each printed electrode 21 (positive electrode 21a and negative electrode 21b) is around 1 to 100 mm. Further, it is preferable that the length W, in the width direction X, of the printing substrate 22 is around 78 to 162 mm, and it is preferable that the length W1, in the X direction, of each printed electrode 21 (positive electrode 21a and negative electrode 21b) is around 3 to 150 mm. Further, it is preferable that the area of each printed electrode 21 (positive electrode 21a and negative electrode 21b) is around 3 to 1500 mm².

It is preferable that the percentage ((L2/L)×100) of the separation distance L2 (see FIG. 4), in the longitudinal direction Y, between the positive electrode 21a and the negative electrode 21b to the length L, in the longitudinal direction Y, of the printing substrate 22 is around 0.18 to 6.6%, and it is preferable that the percentage ((W2/W)×100) of the separation distance (the aforementioned predetermined interval) W2 (see FIG. 4), in the width direction X, between printed electrodes 21 (between the electrode arrays) adjacent to one another in the width direction X to the length W, in the width direction X, of the printing substrate 22 is around 6 to 20%. More specifically, it is preferable that the separation distance L2 (see FIG. 4), in the longitudinal direction Y, between the positive electrode 21a and the negative electrode 21b is around 1 to 25 mm, and it is preferable that the separation distance W2 (see FIG. 4), in the X direction, between printed electrodes 21 (the arrays) adjacent to one another in the X direction is around 5 to 15 mm.

By forming the planar printed electrodes 21 by applying the electroconductive ink on the surface of the printing substrate 22 in, for example, a lattice form having non-application sections as illustrated in FIG. 5(b), the amount of electroconductive ink used can be reduced, and cost reduction can be achieved. The shape, size, and mutual arrangement/positioning of the planar printed electrodes 21 are not limited to those of the present embodiment, and can be designed as appropriate.

Further, in the present embodiment, like the printed electrodes 21, the conducting wire portions 23 (conducting wire portions 23a, 23b1, 23b2) for connecting the respective electrode groups, each including four planar printed electrodes 21, to the respective terminal portions 24 (terminal portions 24a, 24b) are formed by the printed electroconductive layer 28 (see FIGS. 3(a) and 3(b)) formed by the electroconductive ink applied to the surface of the printing substrate 22. By forming the conducting wire portions 23 (conducting wire portions 23a, 23b1, 23b2) by the printed electroconductive layer 28 formed by the electroconductive ink, the conducting wire portions 23 (conducting wire portions 23a, 23b1, 23b2) can be provided easily to the backsheet 11b of the urine absorption pad 11 while arranging the printed electrodes 21 so as to be connected to the terminal portions 24 (terminal portions 24a, 24b).

Further, in the present embodiment, a metal snap having electroconductivity is used for the terminal portion 24 (terminal portion 24a, 24b). As illustrated in FIG. 3(b), the metal snap 24 is constituted by a female hook 241 and a male hook 242. The female hook 241 and the male hook 242 are fit together in a state where the cover sheet 27, the conducting wire portions 23, and the printing substrate 22 are sandwiched between the female hook 241 and the male hook 242 in the thickness direction Z. The terminal portion 24 (terminal portion 24a, 24b) may be made by using any one of a metal connector, a zipper, a hook-and-loop fastener (e.g. Magic Tape (registered trademark)), a screw, a hook, or a meshing-type fastening means.

In the present embodiment, the planar printed electrodes 21 and the conducting wire portions 23 (the printed electroconductive layer 28) constituting the urination sensor 20 are formed by applying the electroconductive ink to the surface of the printing substrate 22 according to a predetermined arrangement/form (see FIG. 7(a)).

The printing substrate 22 is formed by using a polyethylene terephthalate film, preferably having a thickness of from 35 to 75 μm for example, which is an electrically insulating resin film having physical properties that can withstand shrinking at the time of drying the applied electroconductive ink. The printing substrate 22 has physical properties that can withstand shrinking at the time of drying the applied electroconductive ink, and can be formed by using a material, as an electrically insulating resin film, having a melting point of 200° C. or higher, with preferable examples including polyethylene terephthalate and polyimides. The printing substrate may be sparingly liquid-permeable. "Sparingly liquid-permeable" refers to a property that does not allow passage of liquid such as water, but allows passage of gas such as water vapor.

For the electroconductive ink to be applied to the printing substrate 22, it is possible to use a material obtained by blending, for example, a carbon powder or a metal powder such as silver or copper, as an electroconductive substance, to an ink which is a mixture including, for example, a dispersing agent, a binder, resin, and a curing agent. The present embodiment employs an electroconductive ink in which a silver powder is blended as a preferable metal powder.

When applying the electroconductive ink to the printing substrate 22 to form the planar printed electrodes 21 and the conducting wire portions 23 by the printed electroconductive layer 28, the electroconductive ink may be printed (applied) only once, but from the viewpoint of increasing the sensitivity for detecting urination, the electrodes and the conducting wire portions may be formed by overlaying and printing (applying) the ink a plurality of times. In this case, it is preferable to perform overlaying and printing one to ten times. As for the method for applying and printing the electroconductive ink, it is possible to employ one of various known methods such as inkjet printing, rotary printing, flexographic printing, screen printing, or gravure printing.

In the present embodiment, substantially the entirety of the printing substrate 22 in regions other than the printed electrodes 21 and the conducting wire portions 23 is omitted by being removed in a later-described cutting step (see FIG. 7(b)). The removed-and-omitted sections, more specifically, the regions between the positive electrodes 21a and the negative electrodes 21b forming the sensor elements 20a—i.e., the sections other than the printed electrodes 21 and the conducting wire portions 23 where the printing substrate 22 is not present—form air-passage openings 25 which retain an air-passage function with later-described non-application sections 26a where the adhesive 26 is not applied (see FIG. 4). The polyethylene terephthalate film constituting the printing substrate 22 is not air-permeable. However, the air-passage openings 25, which are formed by cutting the film, can suppress deterioration of air permeability of the urine absorption pad 11's backsheet 11b to which the urination sensor 20 is attached. It should be noted that the printed electrodes 21 and the conducting wire portions 23 may first be printed on the printing substrate 22 according to a desired printing pattern, and then sections where the electroconductive ink is not applied may be cut. Alternatively, the electroconductive ink may be printed in advance onto the entire surface of the printing substrate 22 made of a resin film, and then the printed electrodes and the conducting wire portions may be formed by cutting the printing substrate 22, to which the electroconductive ink has been printed, into a shape according to a desired printing pattern. The periphery of the air-passage opening 25, serving as air-passage regions, only needs to be substantially surrounded by a rim, and a portion of the peripheral rim may be discontinuous.

It is preferable that the air-passage openings 25 are formed in a region occupying 10% or greater, more preferably 25% or greater, of a surrounding region formed by connecting the outer contour of the printing substrate 22. Further, the air-passage opening 25 is present between two electrodes (positive electrode 21a and negative electrode 21b) adjacent to one another in the longitudinal direction Y and constituting the urination sensor 20. More specifically, it is preferable that the air-passage openings are provided within a region substantially surrounded by the positive electrodes 21a, the negative electrodes 21b and the conducting wire portions 23a, 23b1, 23b2 from the viewpoint of retaining air permeability of the backsheet 11b.

In the present embodiment, the urination sensor 20, which includes the plurality of planar printed electrodes 21 and the printed electroconductive layer 28 formed by applying the electroconductive ink to the printing substrate 22, is bonded to the surface of the backsheet 11b of the urine absorption pad 11 by using a cover sheet 27 made of an air-permeable nonwoven fabric. By covering the urination sensor 20 with the air-permeable cover sheet 27, the air-passage openings 25, where an air-passage function is retained through non-application sections 26a where no adhesive 26 is applied in the cover sheet 27, are formed in the urination sensor 20 in sections where the printing substrate 22 is not present—i.e., in sections except for the printing substrate 22 in the urination sensor 20. It is preferable that, on the non-skin-facing surface side of the backsheet 11b (on the side where the cover sheet 27 is to be bonded), a marking for accurately bonding the cover sheet 27 to the backsheet 11b is printed in a position where the cover sheet 27 is to be bonded.

The printed electrodes 21 and the printed electroconductive layer 28 are attached, together with the printing substrate 22, to the backsheet 11b by using the cover sheet 27 in a state where they are placed in tight contact with a surface (surface on the opposite side from the skin-facing surface side) of the backsheet 11b of the urine absorption pad 11. As described above, an adhesive 26 is applied to a surface of the cover sheet 27 that comes into contact with the backsheet 11b Stated differently, the adhesive 26 is applied to the cover sheet 27 on the inside surface thereof, which is the skin-facing surface side. By causing the adhesive 26 to bond to the backsheet 11b of the urine absorption pad 11 through the air-passage openings 25—which are formed in the removed-and-omitted sections of the printing substrate 22 and on the outside of the outer periphery of the printing substrate 22, the cover sheet 27 is attached so as to cover the urination sensor 20 in a state where the urination sensor 20 is sandwiched between the cover sheet and the backsheet 11b. According to the aforementioned configuration, the urination sensor 20—which includes the printing substrate 22, the plurality of planar printed electrodes 21 formed by the electroconductive ink, the conducting wire portions 23 constituted by the printed electroconductive layer 28 formed by the electroconductive ink, and the terminal portions 24—is superposed on and provided to the backsheet 11b along the backsheet 11b of the urine absorption pad 11 in a state where the printed electrodes 21 are in tight contact with the surface of the backsheet 11b of the urine absorption pad 11.

In the present embodiment, for the materials of the backsheet 11b, the topsheet 11a, and the absorbent member 11c of the urine absorption pad 11, it is possible to use, without particular limitation, materials conventionally used in absorbent articles such as disposable diapers, urine absorption pads, and sanitary napkins. For the backsheet 11b, it is possible to use, for example, an insulating, sparingly liquid-permeable sheet (e.g. a moisture-permeable resin film) used in absorbent articles, or a layered sheet in which a nonwoven fabric made by one of various manufacturing methods (e.g., an air-through nonwoven fabric, a spun-bonded nonwoven fabric, a spun-laced nonwoven fabric, or a needle-punched nonwoven fabric) is layered on the aforementioned insulating sheet. Note that "sparingly liquid-permeable" refers to a property that does not allow passage of liquid such as water, but allows passage of gas such as water vapor. For the topsheet 11a, it is possible to use, for example, a hydrophilic liquid-permeable nonwoven fabric or three-dimensional porous film. For the absorbent core constituting the absorbent member 11c, it is possible to use, for example, a member in which absorbent polymer particles are retained in an aggregate of fibers, such as pulp fibers. For the core-wrap sheet constituting the absorbent member 11c, it is possible to use a hydrophilic sheet, such as a core-wrap sheet made of water-permeable thin paper (tissue paper) or a water-permeable nonwoven fabric.

In the present embodiment, for the nonwoven fabric constituting the cover sheet 27, it is possible to use a material conventionally used in wearable articles, with concrete usable examples including spun-bonded, spun-laced, or air-through nonwoven fabrics. When using a spun-bonded nonwoven fabric, from the viewpoint of processability such as resistance to tearing upon processing, the basis weight is preferably 5 g/m$^2$ or greater, more preferably 10 g/m$^2$ or greater, and, from the viewpoint of thickness, feel, and cost, the basis weight is preferably 100 g/m$^2$ or less, more preferably 80 g/m$^2$ or less. More specifically, the basis weight of the spun-bonded nonwoven fabric is preferably from 5 to 100 g/m$^2$, more preferably from 10 to 100 g/m$^2$, further preferably from 5 to 80 g/m$^2$, and even more preferably from 10 to 80 g/m$^2$. The nonwoven fabric 27 constituting the cover sheet 27 is air permeable. From the viewpoint of moisture permeability, the air permeability is preferably 10 m/kPa·s or greater, more preferably 20 m/kPa·s or greater, and from the viewpoint of strength and adhesiveness, the air permeability is preferably 1500 m/kPa·s or less, more preferably 800 m/kPa·s or less. More specifically, the air permeability of the nonwoven fabric 27 is preferably from 10 to 1500 m/kPa·s, more preferably from 20 to 1500 m/kPa·s, further preferably from 10 to 800 m/kPa·s, and even more preferably from 20 to 800 m/kPa·s. The air permeability is found as the inverse of airflow resistance which is measured by an Automatic Air-Permeability Tester KES-F8-AP1 (air permeability tester) from Kato Tech Co., Ltd. For a material with a low air permeability, the value can also be found from the measurement value of a Gurley densometer.

In the present embodiment, for the adhesive 26 applied to the cover sheet 27, it is possible to preferably use an adhesive for use with the skin and underwear. Examples of such adhesives include acrylic-based adhesives and rubber-based adhesives, and it is possible to preferably use a rubber-based adhesive.

In the present embodiment, for the application pattern including non-application sections 26a where the adhesive 26 is not applied, it is possible to employ one of known application patterns such as spiral-shaped, summit-shaped, omega-shaped, curtain-shaped or stripe-shaped application patterns. In the present embodiment, from the viewpoint of ensuring air permeability and from the viewpoint of adhesiveness for fixing the printing substrate to the wearable article, it is preferable to use, from among the above options, an application pattern employing a spiral spray. By applying the adhesive 26 to the cover sheet 27 according to an application pattern in which there are non-application sections 26a in the air-passage openings 25, it is possible to suppress deterioration in air permeability of the backsheet 11b of the urine absorption pad 11 to which the urination sensor 20 is attached, because passage of air is permitted at least through the non-application sections 26a in the air-passage openings 25 in the printing substrate 22, even in cases where the adhesive 26 is not air-permeable.

As illustrated in FIG. 4, in the present embodiment, the urine absorption pad 11 includes a data collection unit 30 that acquires changes in impedance by applying a voltage that changes periodically with time i.e., a voltage having an alternating-current component to the plurality of positive electrodes 21a and the plurality of negative electrodes 21b (i.e., the plurality of sensor elements 20a) of the urination sensor 20. In the present embodiment, the data collection unit 30 acquires changes in impedance by applying a rectangular-wave voltage with a predetermined frequency.

Figure 6:
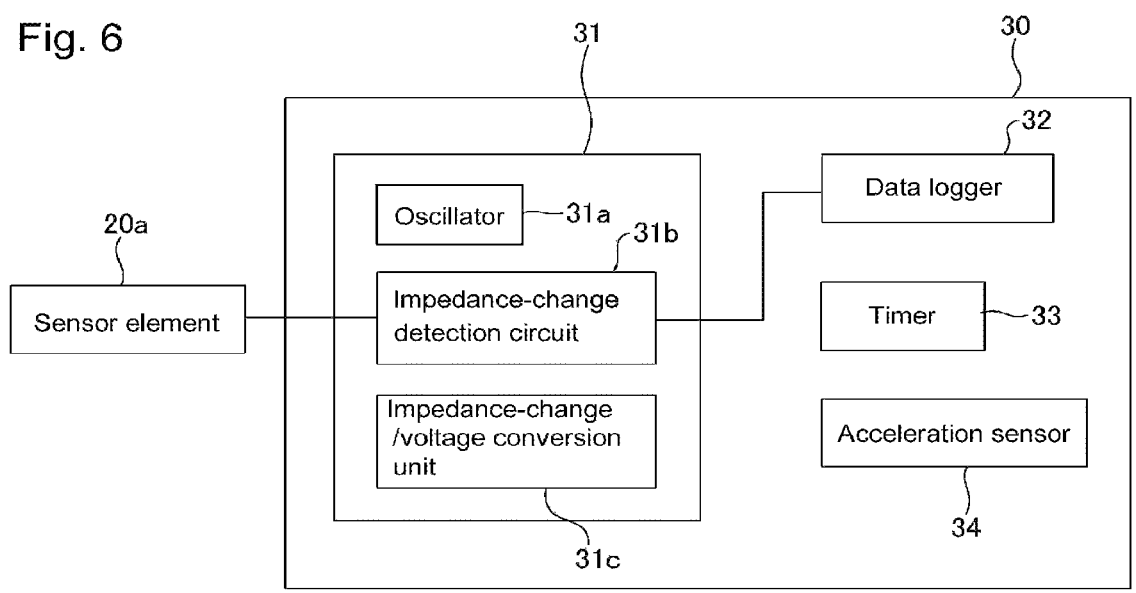
FIG. 6 is a block diagram of a data collection unit that detects and acquires changes in impedance.

As illustrated in FIG. 6, the data collection unit 30 includes: an impedance detection unit 31 that detects changes in impedance; a data logger 32 that stores impedance change data detected by the impedance detection unit 31; a timer 33 that outputs time data; and an acceleration sensor 34 that detects displacements in the wearer's posture.

The impedance detection unit 31 applies a rectangular-wave voltage of around 300 to 1500 KHz within a range of 0 to 5 V to the entire circuit constituted by the plurality of sensor elements 20a of the urination sensor 20 attached to the urine absorption pad 11, and detects changes in impedance of the plurality of sensor elements 20a. More specifically, as illustrated in FIG. 6, the impedance detection unit 31 includes: an oscillator 31a that oscillates a predetermined frequency signal; an impedance-change detection circuit 31b that detects changes in impedance of the entirety of the sensor elements 20a by using the frequency signal from the oscillator 31a; and an impedance-change/voltage conversion unit 31c that converts the changes in impedance detected by the impedance-change detection circuit 31b into voltage-change data.

For example, the impedance-change detection circuit 31b can be achieved by constructing a bridge circuit by employing impedance Zx of the sensor elements 20a of the urination sensor 20 and impedance elements Z1 to Z3 with known impedances. In the impedance detection unit 31, the oscillator 31a is used to apply a predetermined frequency signal (e.g., a 600 KHz rectangular wave between 0 and 1.8 V) to the input terminal of the impedance-change detection circuit 31b. The impedance-change/voltage conversion unit 31c detects a difference in voltage between the divided voltage by the impedance elements Z1 and Z2 and the divided voltage by the impedance element Z3 and the impedance Zx of the sensor elements 20a, and outputs, to the data logger 32, voltage data of a voltage value corresponding to the magnitude of the impedance Zx.

The acceleration sensor 34 is preferably a triaxial acceleration sensor. The acceleration sensor 34 detects respective voltage data, corresponding to the inclination of the data collection unit 30, of accelerations in the X-axis direction, the Y-axis direction, and the Z-axis direction caused by displacements in the posture of the wearer wearing the sensor-equipped wearable article 10, and outputs, to the data logger 32, the voltage data together with time data outputted from the timer 33.

The voltage data (the voltage data corresponding to the magnitude of the impedance Zx and the voltage data corresponding to the inclination of the data collection unit 30) outputted to the data logger 32 are preferably outputted, per unit time, and stored together with time data outputted from the timer 33. The unit time for outputting is preferably from 0.1 to 60 seconds, more preferably from 0.1 to 10 seconds.

The data logger 32 is a device for storing data acquired from the impedance detection unit 31 and the acceleration sensor 34. The data logger 32 is configured so as to transmit, in a wireless or wired manner, stored data to a later-described urination management device 40, which detects whether or not the wearer has urinated and/or measures the urination amount etc., in response to a request from the urination management device 40 or upon detecting connection with the urination management device 40. In the present embodiment, the data logger 32 wirelessly transmits, to the urination management device 40 together with respective time data, voltage data of a voltage value corresponding to the magnitude of the impedance Zx and respective voltage data corresponding to the inclination of the data collection unit 30 in the X-axis direction, the Y-axis direction, and the Z-axis direction caused by displacements in the posture of the wearer.

The data collection unit 30 also includes a power supply (a battery in the present embodiment) for generating the voltage to be applied to the printed electrodes 21 (the positive electrodes 21a and the negative electrodes 21b). As illustrated in FIG. 4, the data collection unit 30 is attached to the urination sensor 20 so as to cover the terminal portions 24a, 24b. In the present embodiment, the data collection unit 30 applies a voltage to the positive electrode 21a via the terminal portion 24a. The data collection unit 30 is attached with two hooks (not illustrated) engageable to the terminal portions 24a, 24b, and thereby the position of the data collection unit 30 with respect to the urination sensor 20 is fixed. By fixing the position of the data collection unit 30 with respect to the urination sensor 20, it becomes easy to detect the wearer's posture by the acceleration sensor 34.

The urine absorption pad 11 with the aforementioned configuration, to which the urination sensor 20 and the data collection unit 30 are attached, can be formed easily and efficiently according to the following manufacturing steps illustrated in FIGS. 7(a) to 7(e). More specifically, in order to form the urine absorption pad 11 to which the urination sensor 20 is attached, first, in an ink application step, the electroconductive ink is applied to the surface of the printing substrate 22 so as to form a predetermined arrangement and shape including sixteen planar printed electrodes 21 and a plurality of printed electroconductive layers 28 connecting the printed electrodes 21 and the terminal portions 24a, 24b (see FIG. 7(a)). After the applied electroconductive ink has dried, in a cutting step, the air-passage openings 25 are formed by cutting and removing preferably substantially the entirety of, or at least a portion of, regions other than the planar printed electrodes 21 and the printed electroconductive layers 28 preferably applied to the printing substrate 22 (see FIG. 7(b)).

Next, the urination sensor 20, which is made of the non-removed sections, is flipped over so that the applied printed electrodes 21 and the printed electroconductive layers 28 are arranged on the lower side and the printing substrate 22 is arranged on the upper side (see FIG. 7(c)). Then, in a cover sheet attachment step, the cover sheet 27 is attached, by means of the adhesive 26 applied to the cover sheet 27, so as to cover the printing substrate 22 provided with the planar printed electrodes 21 and the printed electroconductive layers 28. Next, the terminal portion 24a for the positive electrode 21a and the terminal portion 24b for the negative electrode 21b are attached at predetermined positions connecting with the conducting wire portions 23 created by the printed electroconductive layers 28 (see FIG. 7(d)). Then, the cover sheet 27 is bonded to the urine absorption pad 11's backsheet 11b by means of the applied adhesive 26 in sections extending outside the urination sensor 20 and in sections of the air-passage openings 25 in the printing substrate 22, and thereby, the urination sensor 20 covered by the cover sheet 27 is attached to the urine absorption pad 11 together with the cover sheet 27 (see FIG. 7(e)). At this time, by bonding the cover sheet 27 in alignment with a marking (not illustrated) provided on the backsheet 11b and indicating the position where the cover sheet 27 is to be bonded, the cover sheet 27 can be bonded easily and accurately to the backsheet 11b. Further, the data collection unit 30 is fixed via the terminal portion 24a of the positive electrode 21a and the terminal portion 24b of the negative electrode 21b. In this way, the urination sensor 20 is attached to the urine absorption pad 11 in a manner sandwiched between the cover sheet 27 and the backsheet 11b. Stated differently, the urine absorption pad 11 is formed in a state where the plurality of planar positive electrodes 21a and planar negative electrodes 21b (plurality of sensor elements 20a) are covered and sandwiched by both the backsheet 11b, which is an insulating sheet, and the printing substrate 22, which is an insulating substrate (insulating film).

After forming the urine absorption pad 11 to which the urination sensor 20 has been attached, the urine absorption pad 11 is attached so as to be superposed on the skin-facing surface side (inner side) of the diaper main body 12, as described above. Note that the diaper main body 12 may be a disposable diaper, but may instead be another type of absorbent article, or underwear such as briefs, undershorts, girdles, paper underpants, or adult pull-up pants.

Figure 8:
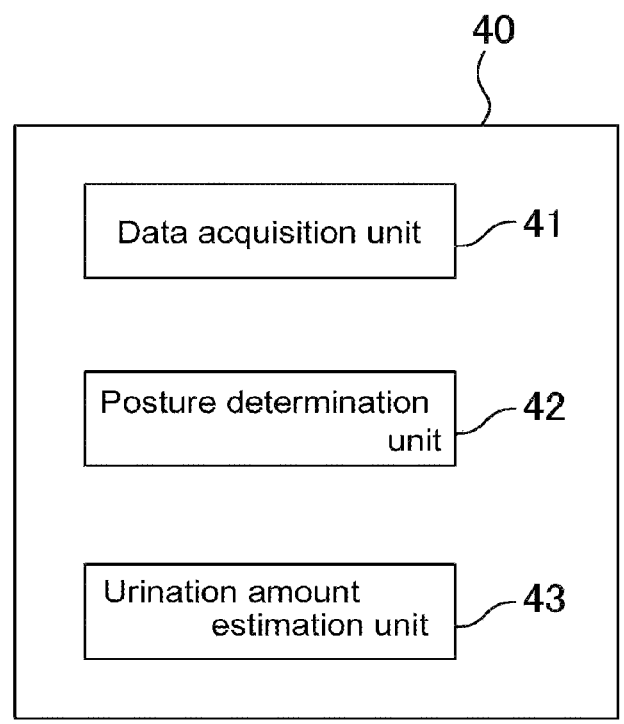
FIG. 8 is a block diagram of a urination management device for detecting whether a wearer has urinated and for measuring the urination amount on the basis of data transmitted from the data collection unit of the sensor-equipped wearable article according to a preferred embodiment of the present invention.

FIG. 8 illustrates a block diagram of a urination management device 40 that detects whether or not the wearer of the sensor-equipped wearable article 10 has urinated and/or measures the urination amount etc. on the basis of data transmitted from the data collection unit 30 of the sensor-equipped wearable article 10 according to a preferred embodiment of the present invention. The urination management device 40 is capable of detecting whether or not the wearer has urinated and/or measuring the urination amount etc. on the basis of voltage data of a voltage value corresponding to the magnitude of the impedance Zx and respective voltage data corresponding to the inclination of the data collection unit 30 in the X-axis direction, the Y-axis direction, and the Z-axis direction caused by displacements in the posture of the wearer, the data being transmitted from the data collection unit 30.

The urination management device 40 of the present embodiment is, for example, a computer including a CPU, a ROM, a RAM, a HDD, etc., and as illustrated in FIG. 8, includes a data acquisition unit 41, a posture determination unit 42, and a urination amount estimation unit 43.

The data acquisition unit 41 is logically connectable, in a wired or wireless manner, to the data collection unit 30 of the sensor-equipped wearable article 10, and receives data outputted from the data logger 32 of the data collection unit 30 when logically connected to the data collection unit 30. In the present embodiment, the data acquisition unit 41 receives voltage data of a voltage value corresponding to the magnitude of the impedance Zx and respective voltage data corresponding to the inclination of the data collection unit 30 in the X-axis direction, the Y-axis direction, and the Z-axis direction caused by displacements in the posture of the wearer, the data being outputted from the data collection unit 30.

The posture determination unit 42 determines the state of the wearer—for example, whether the wearer is lying face down, face up, sideways, or sitting up—from data related to the wearer's posture (voltage data corresponding to the inclination of the data collection unit 30 in the X-axis direction, the Y-axis direction, and the Z-axis direction caused by displacements in the posture of the wearer) obtained by the acceleration sensor 34 as received by the data acquisition unit 41.

The urination amount estimation unit 43 estimates the urination amount from data related to changes in impedance as outputted by the sensor elements 20a of the urination sensor 20 and inputted to the data acquisition unit 41 (i.e., voltage data of a voltage value corresponding to the magnitude of the impedance Zx) and the wearer's posture determined by the posture determination unit 42. In the present embodiment, the urination amount estimation unit 43 detects the spreading of urine on the basis of voltage data of a voltage value corresponding to the magnitude of the impedance Zx outputted from the sensor elements 20a, and estimates the urination amount from the spreading of urine and the wearer's posture. More specifically, the urination amount estimation unit 43 stores, in advance, the voltage value of the sensor elements 20a in a state where there is no urine, and determines that there was urination when the voltage drops from that in a state where there is no urine. Further, the urination amount estimation unit determines the spreading of urine on the basis of the amount of change in data corresponding to the change in impedance at the time of determining urination. Further, from the spreading of urine which has been determined and a plurality of urination amount calculation equations stored in advance in the RAM, the urination amount estimation unit 43 selects a urination amount calculation equation corresponding to the wearer's posture as determined by the posture determination unit 42, and estimates the urination amount at the time of measurement by using the corresponding urination amount calculation equation. In this way, the urination management device 40 can estimate the urination amount of the wearer wearing the sensor-equipped wearable article 10.

Note that, instead of outputting the urination amount as a numerical value, the urination amount estimation unit 43 may estimate the urination amount by outputting, in stages, a relative amount for example, indicating that the amount is smaller or greater—with respect to the total absorption capacity of the sensor-equipped wearable article 10.

The sensor-equipped wearable article 10 of the present embodiment adopts a configuration of attaching, to the backsheet, the urination sensor 20 including the planar printed electrodes 21 formed by applying the electroconductive ink to the printing substrate 22. Thus, sheet shrinkage is prevented at the time of drying the electroconductive ink. Therefore, variations in the detection of urination amount by the urination sensor 20 can be effectively suppressed, and also, the urination sensor 20 using the electroconductive ink can be provided easily.

More specifically, in the present embodiment, the urination sensor 20 includes: a printing substrate 22 made of a resin film; and a plurality of planar printed electrodes 21 (positive electrodes 21a and negative electrodes 21b) that constitute sensor elements 20a and that are made by an electroconductive ink applied to a surface of the printing substrate 22. The electroconductive ink is not directly applied to the one sheet, such as the urine absorption pad 11's backsheet 11b, among the plurality of sheets constituting the wearable article 10, but is applied to the printing substrate 22, thereby forming the planar printed electrodes 21. The formed printed electrodes 21 are provided to the wearable article 10 by being bonded to, for example, the backsheet 11b together with the printing substrate 22. The printing substrate 22 made of a resin film, preferably a polyethylene terephthalate film etc., to which the electroconductive ink is applied has physical properties that can withstand shrinking at the time of drying the applied electroconductive ink. Thus, by providing the planar printed electrodes 21 to the backsheet 11b by means of the printing substrate 22, the backsheet 11b is prevented from shrinking at the time of drying the electroconductive ink. Accordingly, the urination sensor 20, including the printed electrodes 21 formed by using the electroconductive ink, can be provided to the backsheet 11b, which is one of the plurality of sheets constituting the wearable article 10, easily and efficiently according to the aforementioned manufacturing steps, for example.

Further, the printing substrate 22 made of a resin film, such as a polyethylene terephthalate film, to which the electroconductive ink is applied has physical properties that are less likely to stretch compared to nonwoven fabrics. Thus, using the urination sensor 20—which includes the plurality of planar printed electrodes 21 provided by applying the electroconductive ink to the printing substrate 22—by attaching the sensor to the wearable article 10 makes it possible, for example, to keep the separation distance L2 (see FIG. 4) between the planar positive electrode 21a and the planar negative electrode 21b constant, thereby allowing stable detection of changes in impedance and also effectively suppressing variations in detection of the urination amount by the urination sensor 20.

Further, the sensor-equipped wearable article 10 of the present embodiment adopts a configuration wherein: the urination sensor 20—which includes the planar printed electrodes 21 formed by applying the electroconductive ink to the printing substrate 22 made of a resin film—is attached to the backsheet 11b; and changes in impedance between the planar positive electrodes 21a and the planar negative electrodes 21b are detected by preferably applying a rectangular-wave voltage of a predetermined frequency to the planar printed electrodes 21 of the urination sensor 20. Thus, the urination amount can be detected with higher accuracy compared to methods in which urination is detected, for example, by causing the printed electrodes 21 to short-circuit.

More specifically, in the present embodiment, the printing substrate 22 made of a resin film, such as a polyethylene terephthalate film, to which the electroconductive ink is applied has electrically insulating properties. Thus, the planar printed electrodes 21 are sandwiched between the electrically insulating printing substrate 22 and the electrically insulating backsheet 11b, and thereby the top side and the back side of the printed electrodes 21 are covered, thereby allowing the planar printed electrodes 21 to be electrically insulated from the exterior of the urination sensor 20 in terms of direct current. By insulating the printed electrodes 21 in terms of direct current, changes in capacitance between the electrodes can be detected, in contrast to, for example, wearable articles including electrodes (sensors) detecting urination by directly contacting urine, and as a result, changes in impedance between the electrodes can be detected. Particularly, by applying a voltage that changes periodically with time and detecting high-frequency imped-ances, changes in impedance can be detected with high accuracy, thereby allowing the urination amount to be detected with high accuracy. Further, the backsheet 11b is sparingly liquid-permeable, and the printed electrodes 21 are arranged on the outer side, i.e., on the front side, thereof. Therefore, as viewed from the skin side, the printed electrodes 21 are in a state covered by the backsheet 11b. Thus, urine is inhibited from reaching between the electrodes upon urination, and as a result, insulation of direct current is maintained, and thus, changes in capacitance can be detected more accurately. Also from this viewpoint, the urination amount can be detected with high accuracy.

Further, the sensor-equipped wearable article 10 of the present embodiment adopts a configuration wherein the urination sensor 20 has air-passage openings 25 that maintain an air-passage function by the sections where the printing substrate 22 is not present. Thus, for example, even when changes in capacitance between the electrodes are detected in a state where the printed electrodes 21 are electrically insulated from the exterior of the urination sensor 20, the urination amount can be detected with high accuracy without impairing air permeability of the urine absorption pad 11 to which the urination sensor 20 is attached.

More specifically, in the present embodiment, sections where the printing substrate 22 is not present are provided between the plurality of planar printed electrodes 21, which are formed by applying the electroconductive ink to the printing substrate 22 constituting the urination sensor 20. The urination sensor 20, including these sections where the printing substrate 22 is not present, is covered by the cover sheet 27 in which the adhesive 26 is applied to a nonwoven fabric, and the printing substrate 22 is bonded to the urine absorption pad 11's backsheet 11b by the adhesive 26 applied to the cover sheet 27 in a state where the printed electrodes 21 face the surface of the backsheet 11b. Further, on the surface of the cover sheet 27 where the adhesive is applied, there are non-application sections 26a where the adhesive 26 is not applied. Thus, the sections in the urination sensor 20 where the printing substrate 22 is not present are covered by sections of the nonwoven fabric where the adhesive 26 is applied and by the non-application sections 26a where the adhesive 26 is not present. Therefore, at the non-application sections 26a where the adhesive 26 is not applied, air-passage openings 25 that maintain an air-passage function are formed in the urination sensor 20. Accordingly, even if the printed electrodes 21 of the urination sensor 20 are formed by applying the electroconductive ink to the air-impermeable printing substrate 22, the air-passage openings 25—which are located at sections where the printing substrate 22 of the urination sensor 20 is not present—can ensure sufficient air permeability in the urine absorption pad 11 to which the urination sensor 20 is attached and also in the wearable article 10 to which the urine absorption pad 11 is attached. Further, the printed electrodes 21 formed on the printing substrate 22 do not allow the 21 backsheet 11b to cause deformation by shrinking at the time of drying, and thus, the urination amount of urine absorbed by the urine absorption pad 11 can be detected with high accuracy.

Further, the urination sensor 20 is attached integrally together with the cover sheet 27 to the urine absorption pad 11's backsheet 11b by means of the adhesive 26 applied to the cover sheet 27. Thus, the urination sensor 20 is difficult to reuse repeatedly, and therefore, for example, bacterial infection caused by reuse can be avoided, and thus allow the sensor to be used sanitarily.

Figure 9:
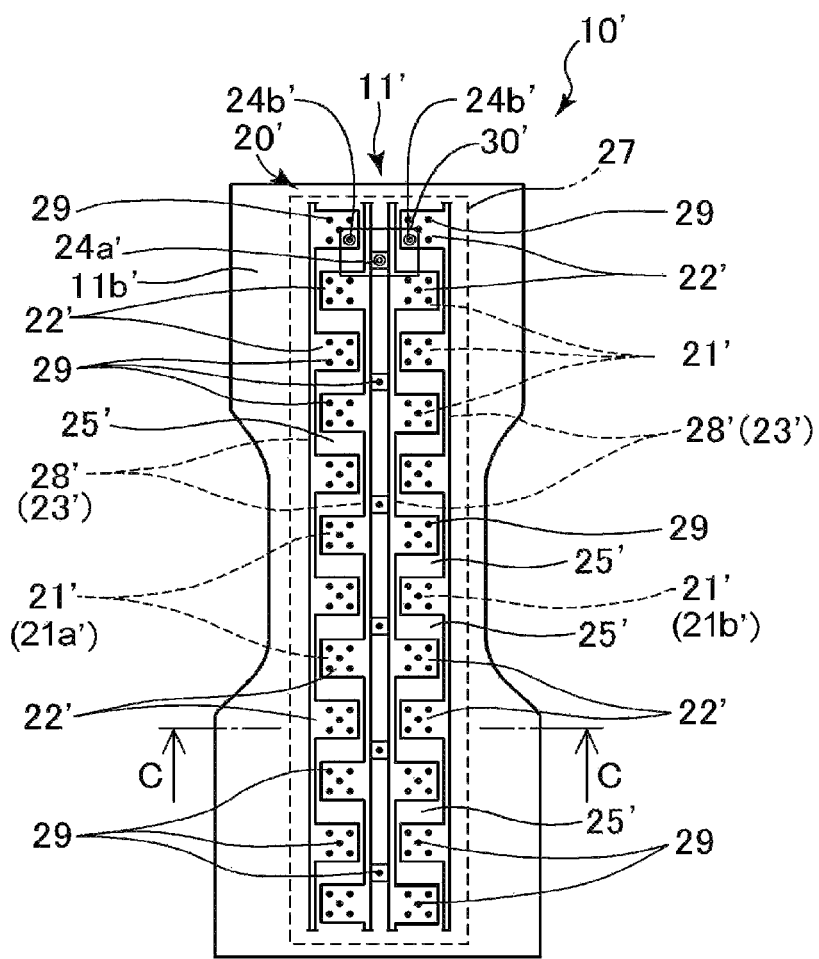
FIG. 9 is a back-side view illustrating an example of another embodiment of a urine absorption pad.

FIG. 9 illustrates another embodiment of a urine absorption pad constituting a sensor-equipped wearable article. The urine absorption pad 11' of the sensor-equipped wearable article 10' illustrated in FIG. 9 has a configuration substantially similar to the urine absorption pad 11 of the foregoing embodiment.

More specifically, a printing substrate 22' made of a resin film, such as a polyethylene terephthalate film, to which the electroconductive ink is applied has electrically insulating properties. Thus, planar printed electrodes 21' are sandwiched between the electrically insulating printing substrate 22' and an electrically insulating backsheet 11b', and thereby the top side and the back side of the printed electrodes 21' are covered.

Further, sections 25' where the printing substrate 22' is not present are provided between the plurality of planar printed electrodes 21', which are formed by applying the electroconductive ink to the printing substrate 22' constituting the urination sensor 20'. The urination sensor 20', including these sections 25' where the printing substrate 22' is not present, is covered by a cover sheet 27 in which an adhesive 26' is applied to a nonwoven fabric, and the printing substrate 22' is bonded to the backsheet 11b' of a urine absorption pad 11' by the adhesive 26' applied to the cover sheet 27 in a state where the printed electrodes 21' face the surface of the backsheet 11b'. Further, on the surface of the cover sheet 27 where the adhesive is applied, there are non-application sections (not illustrated) where the adhesive 26' is not applied. Thus, the sections in the urination sensor 20' where the printing substrate 22' is not present are covered by sections of the nonwoven fabric where the adhesive 26' is applied and by the non-application sections where the adhesive 26' is not present. Therefore, at the non-application sections where the adhesive 26' is not applied, air-passage openings 25' that maintain an air-passage function are formed in the urination sensor 20'.

Further, in the present embodiment, through holes 29 penetrating the planar printed electrodes 21', the printing substrate 22', and the cover sheet 27, which are arranged in a superposed manner, are formed in the section of the urination sensor 20' bonded to the backsheet 11b' of the urine absorption pad 11' by means of the cover sheet 27. Stated differently, in the wearable article 10' according to another embodiment as illustrated in FIG. 9, a plurality of through holes 29 penetrating the printing substrate 22' and the cover sheet 27 are provided in sections (inner portions within the surface) of the planar printed electrodes 21; and the plurality of through holes 29 penetrating the printing substrate 22' and the cover sheet 27 form, in the inner portions within the surface of the planar printed electrodes 21', additional air-passage openings which retain an air-passage function and which are provided in addition to the air-passage openings 25' created by the sections where the printing substrate 22' is not present and provided between the planar printed electrodes 21'.

The through holes 29, which are formed in the sections of the planar printed electrodes 21', are formed at a plurality of positions in each printed electrode 21' as illustrated in FIG. 9, and it is preferable that one to eight through holes are formed per printed electrode 21'. In the present embodiment, five through holes 29 are formed per each printed electrode 21'. The percentage of the total area of the through holes 29 with respect to the area of each printed electrode 21' is preferably around 2% to 74%, and the percentage of the area of each through hole 29 with respect to the area of each printed electrode 21' is preferably around 2 to 9.2%. In the present embodiment, the through holes 29 are each formed in a substantially circular shape, and the diameter of each through hole 29 is preferably around 2 to 4 mm, and the area of each through hole 29 is preferably around 12 to 29 mm².

Also, in the urine absorption pad 11' of the sensor-equipped wearable article 10' illustrated in FIG. 9, conducting wire portions 23' are made of a printed electroconductive layer 28' formed by an electroconductive ink applied to the surface of the printing substrate 22'.

In the urine absorption pad 11' of the sensor-equipped wearable article 10' illustrated in FIG. 9, the aforementioned through holes 29 function as air-passage openings in addition to the air-passage openings 25', and thus, reduction in air permeability—which may otherwise occur by providing the printed electrodes 21', the printing substrate 22', and the printed electroconductive layer 28' is suppressed, and air permeability of the urine absorption pad 11', to which the urination sensor 20' is attached, can be improved more effectively.

Further, in the urine absorption pad 11' of the sensor-equipped wearable article 10' illustrated in FIG. 9, in terms of the terminal portions 24a', 24b' connected to the plurality of planar printed electrodes 21' (or the conducting wire portions that connect the planar printed electrodes 21'), the number of terminal portion(s) 24a' connected to the positive electrodes 21a' is different from the number of terminal portion(s) 24b' connected to the negative electrodes 21b'. More specifically, in the urine absorption pad 11' illustrated in FIG. 9, for example, a terminal portion 24a' for the positive electrodes 21a' is provided at one location and terminal portions 24b' for the negative electrodes 21b' are provided at two locations at the end section in the longitudinal direction Y. Further, in the urine absorption pad 11' illustrated in FIG. 9, the data collection unit 30 has three hooks (not illustrated) corresponding respectively to the terminal portion 24a' for the positive electrodes 21a' provided at one location and the terminal portions 24b' for the negative electrodes 21b' provided at two locations. Since the number of terminal portion(s) 24a' connected to the positive electrodes 21a' and the number of terminal portion(s) 24b' connected to the negative electrodes 21b' are made different from each other and the arrangement thereof is made rotationally asymmetrical, the orientation of a measuring instrument (the aforementioned data collection unit 30) attached to the urine absorption pad 11' by means of the terminal portions 24a', 24b' can be fixed.

In order to improve calculation accuracy at the time of estimating the urination amount on the basis of the detection data of the urination sensor 20', it is important to detect the wearer's posture with the acceleration sensor, estimate the distribution of urine within the urine absorption pad 11, and reflect it to the urination amount calculation. In order to correctly detect the wearer's posture with the acceleration sensor, it is necessary that the orientation of the data collection unit 30, which is the measuring instrument, is fixed when it is attached to the urine absorption pad 11'. By making the number of terminal portion(s) 24a' connected to the positive electrodes 21a' different from the number of terminal portion(s) 24b' connected to the negative electrodes 21b', the attachment direction of the data collection unit 30 attached to the urine absorption pad 11' is fixed, which thereby prevents erroneous detection of the wearer's posture. As a result, calculation accuracy at the time of estimating the urination amount can be improved.

It should be noted that, even when the number of terminal portion(s) 24a' connected to the positive electrodes 21a' is the same as the number of terminal portion(s) 24b' connected to the negative electrodes 21b', the same effect as mentioned above can be obtained by employing a rotationally asymmetrical arrangement or by varying the shapes of the terminal portions 24a', 24b' for the positive electrodes 21a' and the negative electrodes 21b'.

Figure 10:
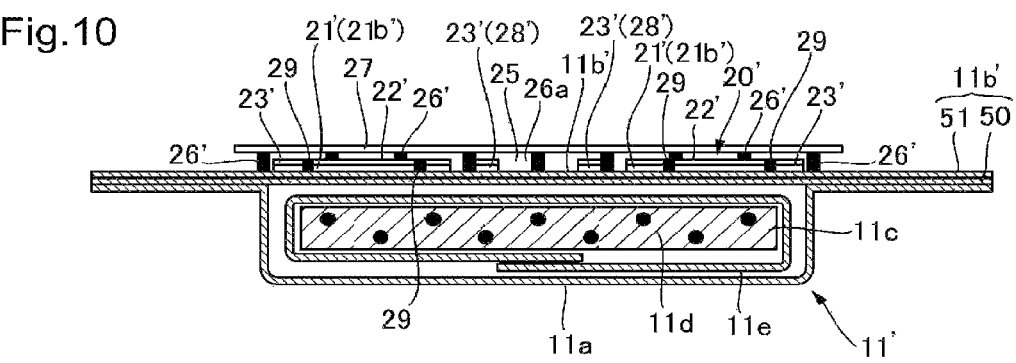
FIG. 10 is an enlarged schematic cross-sectional view taken along line C-C of FIG. 9.

In the urine absorption pad 11' of the sensor-equipped wearable article 10' illustrated in FIG. 9, the backsheet 11b', which is the one sheet, is a layered sheet made by layering a nonwoven fabric on a film, and the surface facing the printed electrodes 21' is formed by the nonwoven fabric. More specifically, in the urine absorption pad 11' of the sensor-equipped wearable article 10' illustrated in FIG. 9, the backsheet 11b' is formed by a layered sheet including a sparingly liquid-permeable sheet 50 used as backsheets in conventional absorbent articles (such as disposable diapers), and a nonwoven fabric sheet 51, as illustrated in FIG. 10. Thus, the nonwoven fabric sheet 51 is arranged so as to be interposed between the printing substrate 22' and the sparingly liquid-permeable sheet 50 of the urine absorption pad 11'. In the urine absorption pad 11' illustrated in FIG. 9, the cover sheet 27 provided so as to cover the printing substrate 22' is bonded to the nonwoven fabric sheet 51 through the air-passage openings 25 between the printed electrodes 21', and thereby, the printing substrate 22' (printed electrodes 21') is arranged in tight contact with the backsheet 11b'. The nonwoven fabric sheet 51, which forms the backsheet 11b', is integrally layered with the sparingly liquid-permeable sheet 50 by, for example, an adhesive applied in a spiral pattern so as to provide air permeability.

By bonding the cover sheet 27, preferably with an adhesive force allowing peeling, to the nonwoven fabric sheet 51 of the backsheet 11b' through the air-passage openings 25' between the printed electrodes 21', the printing substrate 22' can be peeled off from the nonwoven fabric sheet 51 together with the cover sheet 27, for example, after using the sensor-equipped wearable article 10'. In this way, metal parts, such as the terminal portions 24a', 24b' attached to the printing substrate 22', can be separated for disposal.

Further, since the nonwoven fabric sheet 51 is interposed between the sparingly liquid-permeable sheet 50 and the printing substrate 22', a space is retained by the nonwoven fabric sheet 51 between the sparingly liquid-permeable sheet 50 and the printing substrate 22', which makes it possible to avoid deterioration in moisture permeability of the backsheet 11b' caused by direct tight contact between the sparingly liquid-permeable sheet 50 and the printing substrate 22'. Further, this backsheet 11b', which is formed of a layered sheet including the sparingly liquid-permeable sheet 50 and the nonwoven fabric sheet 51, undergoes little shrinkage in high-temperature environments, and there is little difference in shrinkage with the printing substrate 22'. Thus, the printed electrodes 21' do not float up as a result of shrinking of the backsheet 11b' in high-temperature environments, and changes in impedance can be detected in a stable state even in high-temperature environments.

In the urine absorption pad 11' of the sensor-equipped wearable article 10' illustrated in FIG. 9, for the nonwoven fabric constituting the nonwoven fabric sheet 51, it is possible to use a material conventionally used in wearable articles, with concrete examples including spun-bonded, spun-laced, or air-through nonwoven fabrics. In cases of using a spun-bonded nonwoven fabric, the basis weight thereof is preferably 8 g/m$^2$ or greater, more preferably 10 g/m$^2$ or greater, from the viewpoint of the quality of the finished product, and is preferably 30 g/m$^2$ or less, more preferably 20 g/m$^2$ or less, from the viewpoint of air permeability.

Figure 7:
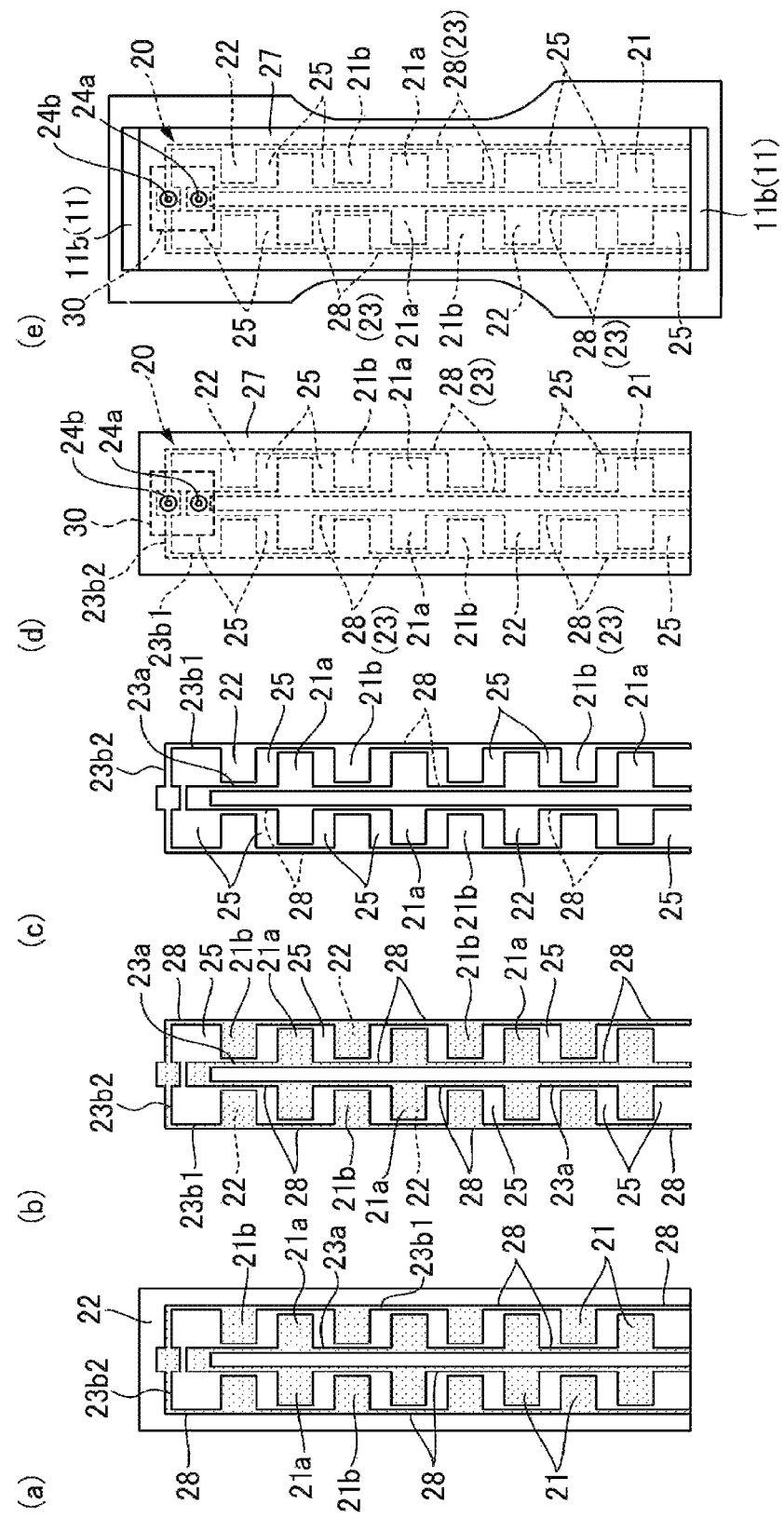
FIGS. 7(a) to 7(e) are schematic plan views illustrating steps for attaching the urination sensor to the urine absorption pad.

The sensor-equipped wearable article 10' illustrated in FIG. 9 can be formed easily and efficiently according to substantially the same manufacturing steps as those for the aforementioned wearable article 10 illustrated in FIGS. 7(*a*) to 7(*e*). More specifically, first, in an ink application step, the electroconductive ink is applied over the entire surface of the printing substrate 22', for example. After the applied electroconductive ink has dried, in a cutting step, unnecessary sections in the printing substrate 22', to which the electroconductive ink has been applied, are cut and removed such that the printed electrodes 21' and the printed electroconductive layer 28' have predetermined shapes. More specifically, unnecessary sections in the printing substrate 22', to which the electroconductive ink has been applied over the entire surface, are punched out and cut such that the printing substrate has a predetermined shape including the printed electrodes 21' and the printed electroconductive layer 28'. By punching out and cutting the unnecessary sections so that the printed electrodes 21' have predetermined shapes, the flexibility of the printing substrate 22' to which the printed electrodes 21' have been applied is improved, and the feel upon use can be improved. Further, by performing cutting after applying the electroconductive ink over the entire surface of the printing substrate 22', no positioning is required with respect to the applied electroconductive ink, and thus, for example, mass production can be performed in a short time, and production efficiency can be improved.

Next, the non-removed sections having predetermined shapes are flipped over so that the applied printed electrodes 21' and the printed electroconductive layer 28' are arranged on the lower side and the printing substrate 22' is arranged on the upper side. Then, in a cover sheet attachment step, the cover sheet 27 is attached, by means of the adhesive applied to the cover sheet 27, so as to cover the printing substrate 22' provided with the printed electrodes 21' and the printed electroconductive layer 28'. In this way, sections constituting the air-passage openings 25' are formed in sections other than the printed electrodes 21' and the printed electroconductive layer 28'. Then, a plurality of through holes 29 are formed on the inner side of the surface of the respective planar printed electrodes 21' so as to penetrate, in the thickness direction, the planar printed electrodes 21', the printing substrate 22', and the cover sheet 27, which are arranged in a superposed manner. By forming the plurality of through holes 29, the through holes 29 in the planar printed electrodes 21' also function as air-passage openings in addition to the air-passage openings 25' between the printed electrodes 21', and thus, reduction in air permeability—which may otherwise occur by providing the planar printed electrodes 21', the printing substrate 22', and the printed electroconductive layer 28'—is suppressed, and reduction in air permeability of the urine absorption pad 11' can be suppressed more effectively.

Then, the urination sensor 20' is formed by attaching the terminal portions 24a', 24b' for the positive electrodes 21a' and the negative electrodes 21b' to the printed electrodes 21' and the conducting wire portions 23' formed by the printed electroconductive layer 28'. Then, the cover sheet 27 is bonded to the nonwoven fabric sheet 51 of the backsheet 11b' by the applied adhesive 26', preferably in sections of the cover sheet 27 extending outside the urination sensor 20' and sections in regions of the cover sheet 27 overlapping the air-passage openings 25'. In this way, the urine absorption pad 11' is formed, wherein: the plurality of positive electrodes 21a' and the negative electrodes 21b' are covered by being sandwiched between the backsheet 11b', which is an insulating sheet, and the printing substrate 22', which is an insulating substrate (insulating film); and the urination sensor 20', including the air-passage openings 25' for retaining air permeability and the plurality of through holes 29 functioning as air-passage openings, is attached thereto.

Like the sensor-equipped wearable article 10 of the foregoing embodiment, the sensor-equipped wearable article 10' according to this other embodiment illustrated in FIG. 9 including the urine absorption pad 11' formed as above, sheet shrinkage is prevented at the time of drying the electroconductive ink. Therefore, variations in the detection of urination amount by the urination sensor 20' can be effectively suppressed, and also, the urination sensor 20' using the electroconductive ink can be provided easily. Further, the urination amount can be detected with high accuracy without impairing air permeability.

It should be noted that the present invention is not limited to the foregoing embodiments and various modifications can be made. For example, the one sheet to which the urination sensor is to be attached does not necessarily have to be the urine absorption pad's backsheet, but it may be another sheet constituting the wearable article and suitable for detecting the wearer's urination. The conducting wire portions connecting the printed electrodes to the terminal portions do not necessarily have to be printed electroconductive portions formed by an electroconductive ink, but they may be other members such as electroconductive threads. Other than singly-used absorbent articles such as urine absorption pads, the wearable article to which the urination sensor is attached may be, for example, a combination of an absorbent article, such as a urine absorption pad, serving as an inner material and a disposable diaper serving as an outer member. Examples of singly-used absorbent articles include disposable diapers (tape-fastening type or pull-on type). The scope of the present invention encompasses cases where an absorbent article that may be used singly is used as an inner member. Examples of outer members used in combination with absorbent articles used as inner members include various underwear, such as briefs, undershorts, girdles, paper underpants, and adult pull-up pants.

In relation to the foregoing embodiments of the present invention, the present invention further discloses the following sensor-equipped wearable articles.

{1} A sensor-equipped wearable article comprising a urination sensor that detects urination and that is attached to an outside surface of one sheet among a plurality of sheets constituting the wearable article, wherein:
  the urination sensor includes
  a printing substrate formed of a resin film, and
  a plurality of planar printed electrodes that constitute a sensor element and that are made by an electroconductive ink applied to a surface of the printing substrate;
  the urination sensor is provided with a section where the printing substrate is not present, the section being provided between the plurality of planar printed electrodes;
  the urination sensor, including the section where the printing substrate is not present, is covered by a cover sheet in which an adhesive is applied to a nonwoven fabric;
  the printing substrate is bonded to the one sheet by the adhesive applied to the cover sheet in a manner that the printed electrodes face the surface of the one sheet;
  the one sheet is an electrically insulating, sparingly liquid-permeable substrate;
  the printing substrate is an electrically insulating substrate;
  the plurality of planar printed electrodes are covered by the one sheet and the printing substrate; and
  non-application sections are present on the surface of the cover sheet to which the adhesive is applied, and the section where the printing substrate is not present forms an air-passage opening which retains an air-passage function with the non-application sections.

{2} The sensor-equipped wearable article as set forth in clause {1}, wherein the one sheet is a backsheet of a urine absorption pad.

{3} The sensor-equipped wearable article as set forth in clause {1} or {2}, wherein:
  the one sheet is a layered sheet made by layering a nonwoven fabric on a film; and
  the surface of the one sheet facing the printed electrodes is formed by the nonwoven fabric.

{4} The sensor-equipped wearable article as set forth in any one of clauses {1} to {3}, wherein:
  a plurality of through holes penetrating the printing substrate and the cover sheet are provided in sections of the planar printed electrodes; and
  the plurality of through holes penetrating the printing substrate and the cover sheet form additional air-passage openings which retain an air-passage function and which are different from the air-passage opening created by the section where the printing substrate is not present and provided between the planar printed electrodes.

{5} The sensor-equipped wearable article as set forth in clause {4}, wherein a plurality of the through holes are provided in each of the plurality of planar printed electrodes.

{6} The sensor-equipped wearable article as set forth in clause {4} or {5}, wherein the percentage of the area of the through holes in each of the printed electrodes is from 2% to 74% of the area of each of the printed electrodes.

{7} The sensor-equipped wearable article as set forth in any one of clauses {4} to {6}, wherein the through hole has a circular opened shape having a diameter of from 2 to 4 mm.

{8} The sensor-equipped wearable article as set forth in any one of clauses {1} to {7}, wherein the resin film forming the printing substrate is a polyethylene terephthalate film.

{9} The sensor-equipped wearable article as set forth in any one of clauses {1} to {8}, wherein the electroconductive ink is an ink made by blending a metal powder as an electroconductive substance.

{10} The sensor-equipped wearable article as set forth in any one of clauses {1} to {8}, wherein the electroconductive ink is an ink made by blending a carbon powder as an electroconductive substance.

{11} The sensor-equipped wearable article as set forth in any one of clauses {1} to {10}, wherein the adhesive is applied according to a spiral-shaped, summit-shaped, omega-shaped, curtain-shaped or stripe-shaped application pattern to the nonwoven fabric in a manner that the non-application sections are present.

{12} The sensor-equipped wearable article as set forth in any one of clauses {1} to {11}, wherein:
  the plurality of planar printed electrodes include positive electrodes and negative electrodes arranged alternately with intervals therebetween; and
  the section where the printing substrate is not present is provided at respective sections of the intervals between the positive electrodes and the negative electrodes.

{13} The sensor-equipped wearable article as set forth in any one of clauses {1} to {12}, wherein:
  the sensor-equipped wearable article includes terminal portions which are connected to the plurality of planar printed electrodes or to conducting wire portions that connect the planar printed electrodes; and the number of the terminal portion(s) connected to the positive electrodes is different from the number of the terminal portion(s) connected to the negative electrodes.

INDUSTRIAL APPLICABILITY

With the sensor-equipped wearable article according to the present invention, it is possible to effectively suppress variations in the detection of urination amounts detected by a urination sensor by preventing sheet shrinkage at the time of drying an electroconductive ink, and it is also possible to easily provide a urination sensor using an electroconductive ink. Further, with the sensor-equipped wearable article according to the present invention, it is possible to detect urination amounts with high accuracy without impairing air permeability.

The invention claimed is:

1. A sensor-equipped wearable article comprising a urination sensor that detects urination and that is attached to an outside surface of one sheet among a plurality of sheets constituting the wearable article, wherein:
   the urination sensor includes
      a printing substrate formed of a resin film, and
      a plurality of planar printed electrodes that constitute a sensor element and that are made by an electroconductive ink applied to a surface of the printing substrate;
   the urination sensor is provided with a section where the printing substrate is not present, the section being provided between the plurality of planar printed electrodes;
   the urination sensor, including the section where the printing substrate is not present, is covered by a cover sheet in which an adhesive is applied to a nonwoven fabric;
   the printing substrate is bonded to the one sheet by the adhesive applied to the cover sheet in a manner that the printed electrodes face the surface of the one sheet;
   the one sheet is an electrically insulating, sparingly liquid-permeable substrate;
   the printing substrate is an electrically insulating substrate;
   the plurality of planar printed electrodes are covered by the one sheet and the printing substrate; and
   non-application sections are present on the surface of the cover sheet to which the adhesive is applied, and the section where the printing substrate is not present forms an air-passage opening which retains an air-passage function with the non-application sections.

2. The sensor-equipped wearable article according to claim 1, wherein the one sheet is a backsheet of a urine absorption pad.

3. The sensor-equipped wearable article according to claim 1, wherein:
   the one sheet is a layered sheet made by layering a nonwoven fabric on a film; and
   the surface of the one sheet facing the printed electrodes is formed by the nonwoven fabric.

4. The sensor-equipped wearable article according to claim 1, wherein:
   a plurality of through holes penetrating the printing substrate and the cover sheet are provided in sections of the planar printed electrodes; and
   the plurality of through holes penetrating the printing substrate and the cover sheet form additional air-passage openings which retain an air-passage function and which are different from the air-passage opening created by the section where the printing substrate is not present and provided between the planar printed electrodes.

5. The sensor-equipped wearable article according to claim 1, wherein the resin film forming the printing substrate is a polyethylene terephthalate film.

6. The sensor-equipped wearable article according to claim 1, wherein the electroconductive ink is an ink made by blending a metal powder as an electroconductive substance.

7. The sensor-equipped wearable article according to claim 1, wherein the adhesive is applied according to a spiral-shaped, summit-shaped, omega-shaped, curtain-shaped or stripe-shaped application pattern to the nonwoven fabric in a manner that the non-application sections are present.

8. The sensor-equipped wearable article according to claim 1, wherein:
   the plurality of planar printed electrodes include positive electrodes and negative electrodes arranged alternately with intervals therebetween; and
   the section where the printing substrate is not present is provided at respective sections of the intervals between the positive electrodes and the negative electrodes.

9. The sensor-equipped wearable article according to claim 1, wherein:
   the sensor-equipped wearable article includes terminal portions which are connected to the plurality of planar printed electrodes or to conducting wire portions that connect the planar printed electrodes; and
   the number of the terminal portion(s) connected to the positive electrodes is different from the number of the terminal portion(s) connected to the negative electrodes.

* * * * *